(12) United States Patent
Kim et al.

(10) Patent No.: US 10,301,645 B2
(45) Date of Patent: May 28, 2019

(54) EXPRESSION VECTOR FOR EXPRESSING HETEROGENEOUS GENE

(71) Applicant: MOGAM BIOTECHNOLOGY INSTITUTE, Yongin-si, Gyeonggi-do (KR)

(72) Inventors: Jung-Seob Kim, Yongin-si (KR); Seongtae Yun, Yongin-si (KR); Heechun Kwak, Yongin-si (KR); Mee Sook Oh, Yongin-si (KR); Sumin Lee, Yongin-si (KR)

(73) Assignee: MOGAM BIOTECHNOLOGY INSTITUTE, Yongin-si (KR)

( * ) Notice: Subject to any disclaimer, the term of this patent is extended or adjusted under 35 U.S.C. 154(b) by 121 days.

(21) Appl. No.: 15/105,663

(22) PCT Filed: Dec. 29, 2014

(86) PCT No.: PCT/KR2014/012976
§ 371 (c)(1),
(2) Date: Jun. 17, 2016

(87) PCT Pub. No.: WO2015/099513
PCT Pub. Date: Jul. 2, 2015

(65) Prior Publication Data
US 2016/0304902 A1  Oct. 20, 2016

(30) Foreign Application Priority Data
Dec. 27, 2013 (KR) .................. 10-2013-0165340

(51) Int. Cl.
C12N 15/85 (2006.01)
C12N 7/00 (2006.01)
C12P 21/00 (2006.01)

(52) U.S. Cl.
CPC .............. *C12N 15/85* (2013.01); *C12N 7/00* (2013.01); *C12P 21/00* (2013.01); *C12N 2710/22043* (2013.01); *C12N 2830/42* (2013.01); *C12N 2830/46* (2013.01); *C12N 2830/60* (2013.01)

(58) Field of Classification Search
None
See application file for complete search history.

(56) References Cited

U.S. PATENT DOCUMENTS

| 2009/0181426 | A1 | 7/2009 | DiLeo | |
| 2010/0226912 | A1* | 9/2010 | Mehtali | C07K 16/00 424/130.1 |
| 2011/0061117 | A1 | 3/2011 | Mermod et al. | |
| 2013/0244280 | A1 | 9/2013 | Parikh et al. | |
| 2013/0323302 | A1 | 12/2013 | Constable et al. | |
| 2014/0038233 | A1* | 2/2014 | Yoon | C12N 15/85 435/69.1 |

FOREIGN PATENT DOCUMENTS

| JP | 2010-501170 A | 1/2010 | |
| JP | 2010-525789 A | 7/2010 | |
| KR | 10-2010-0016540 A | 2/2010 | |
| WO | 2005/040384 A1 | 5/2005 | |
| WO | 2008153366 A2 | 12/2008 | |
| WO | 2009102085 A1 | 8/2009 | |
| WO | 2012134215 A2 | 10/2012 | |
| WO | WO 2013157020 A1 * | 10/2013 | ............. C07K 14/51 |

OTHER PUBLICATIONS

Hanson et al., Blood, 1992, vol. 79 (3) pp. 610-618.*
Suemizu, H. et al. "Mammalian expression vector pmAlbEPintPlauGH DNA, complete sequence," GenBank: AB453180.1 Aug. 16, 2011; [online] https://www.ncbi.nlm.nih.govb/nuccore/AB453180.1; (3 pages total).
Nemeth, M.J., et al., "An Erythroid-Specific Chromatin Opening Element Increases β-Globin Gene Expression from Integrated Retroviral Gene Transfer Vectors", Gene Ther. Mol. Biol., 2004; (B) pp. 475-486 (16 pages total).
Japanese Patent Office: Communication dated Jun. 29, 2017, in counterpart Japanese application No. 2016-543136.
Accession No. M62716, Human CSP-B gene flanking sequence, Database GenBank: M62716.1 [online], Nov. 1, 1994, [retrieved on Jan. 29, 2018], Retrieved from the Internet, URL <https://www.ncbi.nlm.nih.gov/nuccore/M62716>.
Japanese Patent Office, Communication dated Feb. 8, 2018, in counterpart Japanese application No. 2016-543136.
GenBank Accession No. JQ394894, Cloning vector SV40p TV, complete sequence, Dec. 12, 2012.
GenBank Accession No. M62716, Human CSP-B gene flanking sequence, Nov. 1, 1994.
GenBank Accession No. U53602, Cloning vector pCI-nGFP-C656G green fluorescent protein-glucocorticoid receptor (GFP-GR) chimeric protein mRNA, complete cds, Sep. 12, 1996.
International Searching Authority International Search Report for PCT/KR2014/012976 dated Apr. 6, 2015.
Database Geneseq [Online] Dec. 19, 2013 (Dec. 19, 2013), "SV40 early enhancer/promoter, SEQ:4.", XP002772416, retrieved from EBI accession No. GSN: BAX25353, Database accession No. BAX25353 (1 page total).
Database Geneseq [Online] Nov. 22, 2012 (Nov. 22, 2012), "Plasmid pC(F)mEGM(R) sequence, SEQ ID 35.", XP002772417, retrieved from EBI accession No. GSN: BAC10530, Database accession No. BAC10530 (2 pages total).
Database Geneseq [Online] Mar. 14, 2013 (Mar. 14, 2013), "Human alpha 1-antitrypsin locus control region (LCR) AAT1081cr, SEQ 58.", XP002772418, retrieved from EBI accession No. GSN: BAJ93140, Database accession No. BAJ93140 (1 page total).

(Continued)

*Primary Examiner* — Mindy G Brown
(74) *Attorney, Agent, or Firm* — Sughrue Mion, PLLC

(57) ABSTRACT

Provided is an expression vector having an improved ability to express a gene. Also provided are cells transformed by the expression vector and a method for mass-producing a target protein by using the cells. The expression vector contains a simian virus 40 promoter, a scaffold attachment region or matrix attachment region element, and a chimeric intron. The vector shows an improved ability to express a gene, and thus, can attain a significantly increased expression of a heterogeneous gene.

13 Claims, 20 Drawing Sheets

Specification includes a Sequence Listing.

(56) References Cited

OTHER PUBLICATIONS

Database Geneseq [Online] Mar. 14, 2013 (Mar. 14, 2013), "Human albumin gene locus control region (LCR) E61cr, SEQ 61.", XP002772419, retrieved from EBI accession No. GSN: BAJ93143, Database accession No. BAJ93143 (1 page total).
European Patent Office, Communication dated Aug. 4, 2017 issued in counterpart European application No. 14875376.7.

* cited by examiner

EXPRESSION VECTOR FOR EXPRESSING HETEROGENEOUS GENE

CROSS REFERENCE TO RELATED APPLICATIONS

This application is a National Stage of International Application No. PCT/KR2014/012976 filed Dec. 29, 2014, claiming priority based on Korean Patent Application No. 10-2013-0165340 filed Dec. 27, 2013, the contents of all of which are incorporated herein by reference in their entirety.

FIELD OF THE PRESENT INVENTION

The present invention relates to an expression vector for improved gene expression, cells transformed by the expression vector, and a method for mass-producing a target protein by using the transformed cells.

BACKGROUND OF THE PRESENT INVENTION

The production of therapeutic recombinant proteins and antibodies has been conducted by using animal cells in most cases, and the efforts are being made to increase the efficiency of production.

For example, a suspended host cell line which was pre-adapted in a serum-free medium has been used for the fast selection of a high producer cell line. Also, high-expression vectors and high producer cell lines have continuously been developed to remove or shorten the time required for gene amplification. Efforts have also been made to develop an efficient way by using an automated cell selection device in the initial selection of cell lines.

High producer cell lines show the expression levels of 30 to 80 pcd even without gene amplification, and high producer cell lines can be prepared within 4 months by using high-expression vectors based on matrix attachment region (MAR) or ubiquitous chromatin opening element (UCOE) which is similar to MAR.

The recent studies show that vector optimization is necessary to achieve 3 to 5 g/L antibody productivity within six months. Recently, the possibility of productivity enhancement is suggested by the optimization of a MAR element such as dual-MAR, multiple-MAR, trans-MAR, etc., but there is an ongoing need for a stable vector with improved production efficiency which may be obtained by the introduction of 5'UTR or intron element.

SUMMARY OF THE PRESENT INVENTION

Therefore, it is an object of the present invention to provide an expression vector for expressing and producing a target protein in a large amount.

It is another object of the present invention to provide a cell transformed by the above expression vector.

It is still another object of the present invention to provide a method for producing a target protein in a large amount by using the transformed cells.

To achieve an object of the present invention as above, there is provided an expression vector comprising an operably linked simian virus 40 (SV40) promoter, a scaffold attachment region (SAR) or matrix attachment region (MAR) element, and a chimeric intron.

To achieve another object of the present invention as above, there is provided a cell transformed by the above expression vector.

To achieve still another object of the present invention as above, there is provided a method for mass-producing a target protein by culturing the transformed cells.

An expression vector according to the present invention shows superior gene expression as compared to a conventional expression vector, and thus, protein expression of an exogenous gene can be significantly increased.

BRIEF DESCRIPTION OF THE DRAWING

The above and other objects and features of the present invention will become apparent from the following descriptions of the present invention, when taken in conjunction with the accompanying drawings.

DETAILED DESCRIPTION OF THE PRESENT INVENTION

Figure 1:
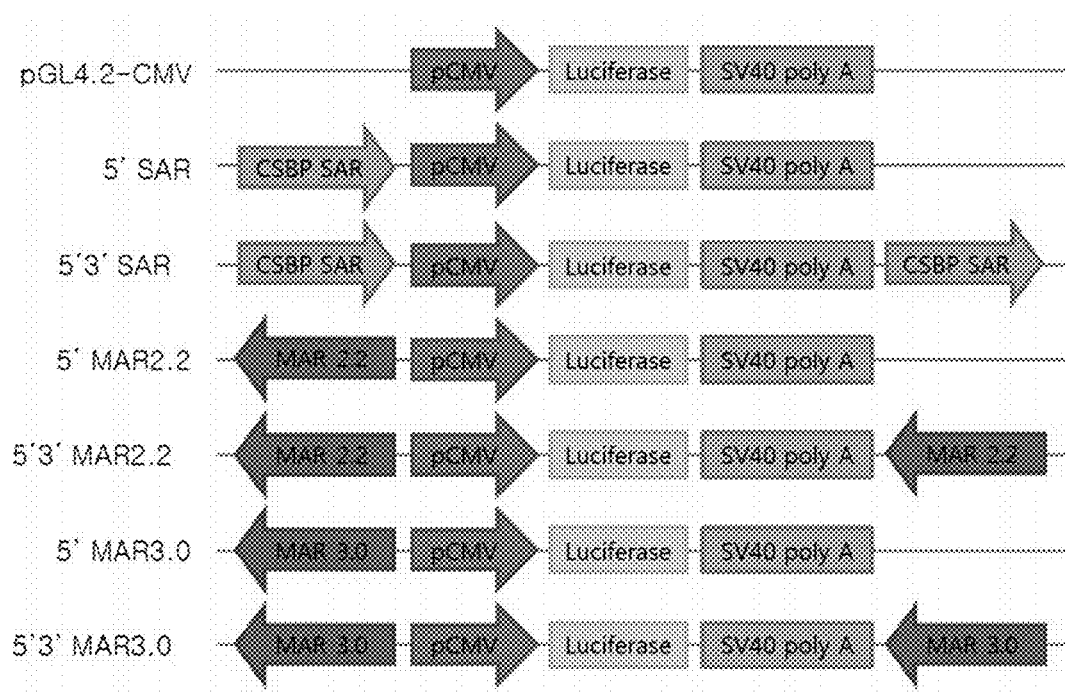
FIG. 1 shows a schematic diagram of luciferase vectors regarding MAR candidate elements.

In the present invention, to prepare a stable expression vector with improved production efficiency for the expression of an exogenous gene in CHO (Chinese Hamster Ovary) cells and the like, elements which can increase the gene expression level are identified among various MAR elements, scaffold attachment region (SAR) elements, locus control regions (LCRs), and intron elements.

Therefore, the present invention provides an expression vector comprising an operably linked simian virus 40 (SV40) promoter, a scaffold attachment region (SAR) or matrix attachment region (MAR) element, and a chimeric intron.

As used herein, the term "promoter" refers to an untranslated nucleic acid sequence upstream of a coding region, which comprises a binding site for a polymerase and which has a transcription initiation activity to mRNA for downstream genes. Specifically, a "promoter" comprises a TATA box or a TATA-like region which serves to initiate transcription by a RNA polymerase; but is not limited to the regions around it; and may comprise such regions that are necessary for the association with proteins other than the RNA polymerase in order to regulate the expression.

In the present invention, a promoter may include a SV40 promoter or its variant, preferably a SV40 promoter represented by SEQ ID NO: 12. A promoter variant refers to a variant in which a certain portion of the promoter sequence is modified by addition, deletion or substitution, in order to increase the gene expression.

According to an embodiment of the present invention, an expression vector of the present invention, which uses a SV40 promoter, shows about 4-fold expression increment as compared to a CMV promoter (see Example 1-1).

In addition, such promoter is operably linked to a target gene, which is a exogenous gene; and as used herein, "operably linked" means that a nucleic acid sequence regulating target gene expression and the nucleic acid sequence encoding a target protein are functionally linked such that they can perform a general function. The operable linkage to a recombinant vector can be implemented using a recombinant DNA technique known in the art; and site-specific DNA cleavage and linkage may be conducted using an enzyme commonly known in the art.

In the present invention, for the gene expression-increasing elements, a SAR or MAR element may be included. The SAR or MAR element may be included to constitute an expression vector such that such element(s) may be present at the 5' end; the 3'end; or both of the 5' and 3' ends of the promoter.

As used herein, a "MAR element" refers to a DNA sequence which temporarily attaches a transcriptionally active DNA loop domain to the nuclear matrix (Pienta et al., (1991) *Crit. Rev. Eukaryotic Gene Expres.*, 1:355-385), and examples of the MAR sequences are known in the art.

In the present invention, in order to select gene expression-increasing elements, dual (5' and 5'+3') and cis+trans related tests were performed using luciferase assay with regard to human beta-globin MAR (Yu, J., Bock, J. H., Slightom, J. L. and Villeponteau, B., Gene 139(2), 139-145 (1994), Genbank No. L22754) and human CSP-B gene flanking SAR (Hanson, R. D. and Ley, T. J., *Blood,* 79(3), 610-618(1992), Genbank No. M62716); and as a result, certain desired elements were selected (see Example 1-1).

The above MAR or SAR element may be a human CSP-B SAR which is represented by SEQ ID NO: 39; MAR2.2, represented by SEQ ID NO: 40 or MAR3.0 represented by SEQ ID NO: 41 isolated from human beta-globin MAR. The SAR or MAR element may be included such that the element(s) may be present at the 5' end; the 3' end; or both of the 5' and 3' ends of the promoter.

According to one embodiment of the present invention, the element may be one designated as 5' MAR2.2, 5' MAR3.0, 3' MAR2.2, 3' MAR3.0, 5'3' MAR2.2 or 5'3' MAR3.0.

An expression vector according to the present invention may comprise a chimeric intron to increase the gene expression.

Such chimeric intron may be represented by SEQ ID NO: 25 (Backliwal, G, Hildinger, M., Chenuet, S., Wulhfard, S., De Jesus, M., Wurm, F. M., *Nucleic Acids Res.,* 36(15), e96 (2008), Genbank No. JQ795930), but the present invention is not limited thereto. In the present invention, the effect on increment of gene expression was confirmed through luciferase assay (see Example 1-3).

According to the present invention, an expression vector comprising both the MAR element and the chimeric intron element shows a synergistic effect on productivity, leading to the increase in the gene expression level (see Example 3-3 and Table 9).

According to one embodiment of the present invention, the novel vector pair II (pMSI-P-ER2LC and pMSI-D-ER2HC) which comprise a MAR element, a SV promoter and a chimeric intron show excellent gene expression-increasing effect as compared to a conventional promoter vectors, a conventional intron vector and the novel vector pair I (pMS-P-D-ER2LC and pMS-ER2HC) which do not contain a chimeric intron.

An expression vector according to the present invention may further comprise a LCR element.

In the present invention, in order to identify gene expression-increasing elements, multimer (×1 and ×4), and dual (5', 3' and 5'+3') related tests were performed using luciferase assay with regard to AAT108 (α-1-antitrypsin precursor, 120 bp, SEQ ID NO: 13) and Alb E6 (serum albumin preproprotein, 81 bp, SEQ ID NO: 14), which previously showed Factor IX expression-increasing effect as disclosed in International Publication No. WO 2009/102085, and as a result, preferred LCR elements were selected (see Example 1-2).

Preferred LCR element in the present invention may be AAT108×4 represented by SEQ ID NO: 15, which may be comprised such that it is present only at the 3' end (3' AAT 108×4); or both of the 5' and 3' ends of the vector (5'3' AAT 108×4). Also, the LCR element may be Alb E6×4 which is represented by SEQ ID NO: 16.

Also, a target gene whose expression is regulated by a promoter may be inserted into an expression vector of the present invention.

The target gene is a gene coding for an exogenous product to be expressed, and may be a gene encoding any type of protein which can be expressed as a recombinant protein. Such target gene comprises a "multiple cloning site (MCS)", which is a nucleic acid sequence having restriction enzyme cleavage sites, so as to be inserted into the vector.

The above target gene may be one of the blood coagulation-related genes and various antibody genes; and may be selected, for example, from the group consisting of factor VII (FVII) gene, factor VIII (FVIII) gene, factor IX (FIX) gene, an epidermal growth factor receptor family antibody gene, insulin gene, interleukin gene, tumor necrosis factor gene, interferon gene, colony stimulating factor gene, chemokine gene, erythropoietin gene, α-fetoprotein gene, a-glucosidase gene, α1-antitrypsin gene, antithrombin gene, lipoprotein gene, celluloplasmin gene, fibrinogen gene, glucocerebrosidase gene, haptoglobin gene, plasminogen gene, prothrombin gene, and transferrin gene, but is not limited thereto. According to one embodiment of the present invention, the target gene may be FIX (factor IX) gene or epidermal growth factor receptor ER2 antibody gene.

The expression vector according to the present invention may comprise any conventionally known transcription terminator. Preferably, it may be connected to polyA. For example, it may comprise SV40 late polyadenylation signal (polyA).

Figure 19:
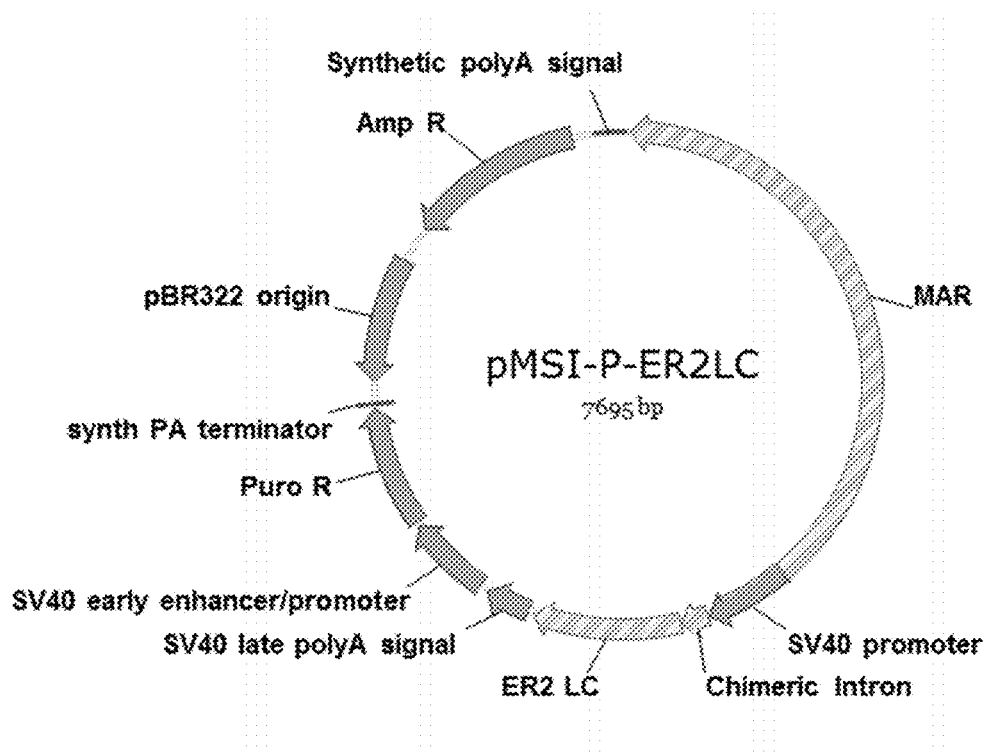
FIG. 19 shows the structures of a second pair of novel vectors ("novel vector pair II") for ER2 antibody expression (pMSI-P-ER2LC and pMSI-D-ER2HC).
Figure 19:
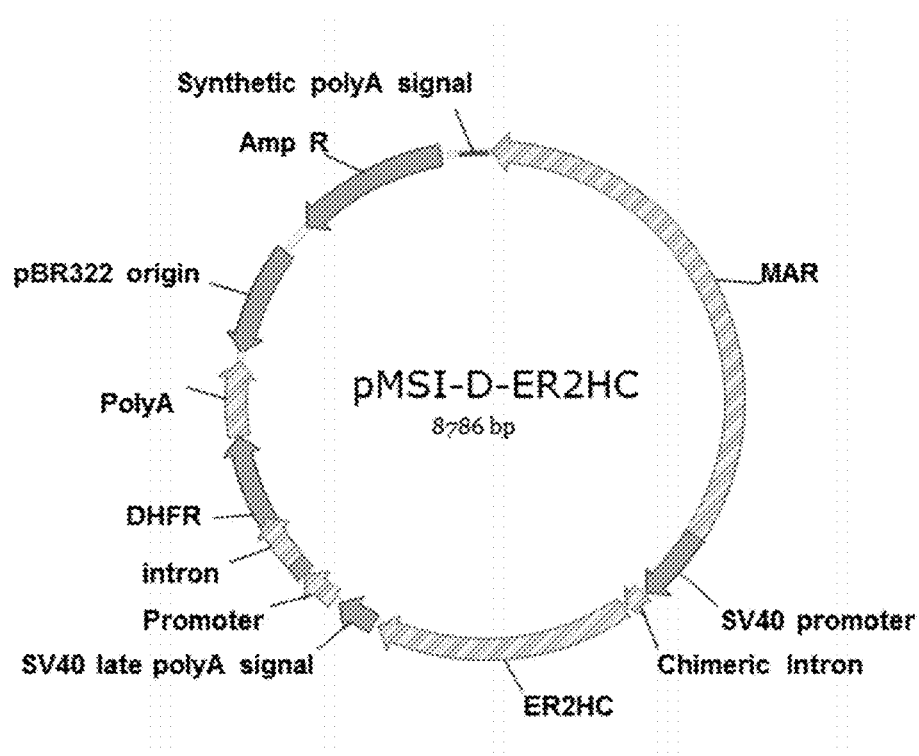

According to one embodiment of the present invention, an expression vector of the present invention has the cleavage map of pMSI-P-ER2LC or pMSI-D-ER2HC shown in FIG. 19. FIG. 19 schematically illustrates an expression vector comprising gene expression-increasing elements such as a MAR element, a chimeric intron element, a SV40 promoter, poly A, etc.

Meanwhile, the present invention provides a cell transformed by the above expression vector.

As used herein, the cell may be an animal cell generally known, and may preferably be selected from the group consisting of CHO-K1 cell, CHO-DG44 cell, CHO—S cell, CHO DUKX-B11 cell, COS3 cell, COST cell, COS1 cell, NSO cell, HeLa cell, Vero cell, PER-C6 cell, HepG2 cell, and BHK cell, but is not limited thereto.

Also, the present invention provides a method for producing a target protein using the above expression vector. More particularly, the present invention provides a method for producing a target protein in a large amount comprising: culturing cells transformed by the above expression vector to express a target protein, and then recovering the target protein.

Such method may comprise the steps of:
(1) inserting a target gene whose expression is regulated by a promoter into the expression vector;
(2) transforming a cell with the expression vector in which the target gene was inserted; and
(3) culturing the cell transformed by the expression vector to express a target protein, and then recovering the target protein.

The method for inserting a target gene, transforming a cell, and culturing the cell to express a target protein, and recovering the target protein may be carried out by using a technique known in the art.

The present invention will be described in more detail with the following Examples. The following Examples are intended to further illustrate the present invention without limiting its scope.

Example 1: Selection of Elements 1-1: MAR Element Selection

In order to improve vectors, MAR of the human β-globin (β-globin MAR, 3 kb, 2.2 kb) and a human CSP-B gene flanking SAR (1.2 kb) were selected as candidates. Also, in order to perform a reporter gene assay which allows indirect evaluation of the protein expression, luciferase assay was chosen considering the convenience of the examination.

It was planned to access the effects of vectors for analysis by comparing the differences in fluorescence values between them and a control vector not containing the MAR element, the vectors for analysis were prepared accordingly. To assess the effects in a stable situation, pGL4.20[luc2/Puro] Firefly luciferase vector (Promega Inc.) was selected, which contains puromycin-resistance gene, a fast and strong cell selection marker.

First, PCR was carried out by using pcDNA3.1(+) vector (Invitrogen, V790-20) as a template, the primer set of SEQ ID NOs: 1 and 2, and a DNA polymerase (Ex-Taq, Takara), to obtain DNA fragments comprising a CMV promoter. Then, the template was denatured at 94° C. for 5 min to separate DNA strands, and the DNA molecules were amplified by repeating a process of denaturing at 94° C. for 30 sec, annealing at 56° C. for 30 sec, and elongation at 72° C. for 1 minute for 30 cycles, followed by additional elongation at 72° C. for 5 min. The DNA fragments amplified by PCR were purified by gel extraction and inserted into pCR2.1-TOPO plasmid vector (Invitrogen, K4500-01). The presence of CMV promoter represented by SEQ ID NO: 11 was verified through a cleavage mapping using restriction enzymes and base sequence analysis, and the CMV promoter was inserted into the NheI/XhoI site in the multiple cloning site of pGL4.20[luc2/Puro] vector. The resulting vector was designated as pGL4.2-CMV and used as a control vector.

Next, using the primer set for SAR (SEQ ID NOs: 3 and 4), the primer set for MAR2.2 (SEQ ID NOs: 5 and 6) and the primer set for MAR3.0 (SEQ ID NOs: 7 and 8), the SAR, MAR2.2 and MAR3.0 were respectively inserted into pCR2.1-TOPO plasmid vectors by the same method as above. The prepared vectors were designated as pCR2.1-SAR, pCR2.1-MAR2.2 and pCR2.1-MAR3.0.

The pMSG and 5'B1-P1 vectors (see Korea Patent No. 408844) were used as the PCR templates for MAR and SAR, respectively. Through a cleavage mapping using restriction enzymes and base sequence analysis, the presence of the SAR, MAR2.2 and MAR3.0 respectively represented by SEQ ID NOs: 39, 40 and 41 were verified. In the subsequent cloning procedure, all inserts were used after cleavage with restriction enzymes and purification through gel extraction; and the vectors were used after cleavage with restriction enzymes and treatment with shrimp alkaline phosphatase.

The insert prepared by cutting pCR2.1-SAR vectors with BamHI was inserted into pGL4.2-CMV vector prepared by cutting with the same restriction enzyme. Through a cleavage mapping using restriction enzymes, the desired SAR DNA fragment was verified to be present in the forward direction, and the resulting vector was designated as pGL4.2-CMV-3'SAR. Next, the inserts prepared by cutting pCR2.1-SAR vector with KpnI and NheI were respectively inserted into pGL4.2-CMV-3'SAR vector and pGL4.2-CMV vector which were cut with the same restriction enzymes. Through a cleavage mapping using restriction enzymes, the presence of the target DNA fragments in each plasmid were verified, and the resulting plasmids were designated as pGL4.2-CMV-5'3'SAR and pGL4.2-CMV-5'SAR, respectively.

To prepare the vectors comprising MAR2.2 and MAR3.0, the inserts prepared by cutting pCR2.1-MAR2.2 and pCR2.1-MAR3.0 with KpnI and NheI, respectively, were inserted into pGL4.2-CMV vectors prepared by cutting with the same restriction enzymes, thereby preparing pGL4.2-CMV-5'MAR2.2 and pGL4.2-CMV-5'MAR3.0 vectors first; and also, the inserts prepared by cutting pCR2.1-MAR2.2 and pCR2.1-MAR3.0 with BamHI were respectively inserted into pGL4.2-CMV-5'MAR2.2 and pGL4.2-CMV-5'MAR3.0 vectors which were prepared by cutting with the same restriction enzyme, to prepare pGL4.2-CMV-5'3'MAR2.2 and pGL4.2-CMV-5'3'MAR3.0 vectors. The MAR element was inserted in a reverse direction. The schematic picture of the prepared luciferase vectors is shown in FIG. 1.

The luciferase expression levels of the vectors with the MAR candidate elements were measured using the adherent cell line CHO-K1. A set of vectors for evaluating Cis+Trans effect were prepared by additionally supplying the above prepared vectors to have 4-fold moles of SAR or MAR element which were also used for the transfection.

Using lipofectamine 2000 (Invitrogen, 11668027), CHO-K1 cell line (ATCC, CCL-61) was transfected with 1.0 μg of the above firefly luciferase vector, and after 48 hrs, cultured with passages in DMEM medium (Lonza, 112-604F) containing puromycin (50 μg/mL) The stable cells were established through the selection period of about 2-4 weeks. The test was carried out in total of 3 sets, and the firefly luciferase analysis was conducted by One-glo luciferase analysis system (Promega, E6110) in which the values were corrected for the number of cells.

Figure 2:
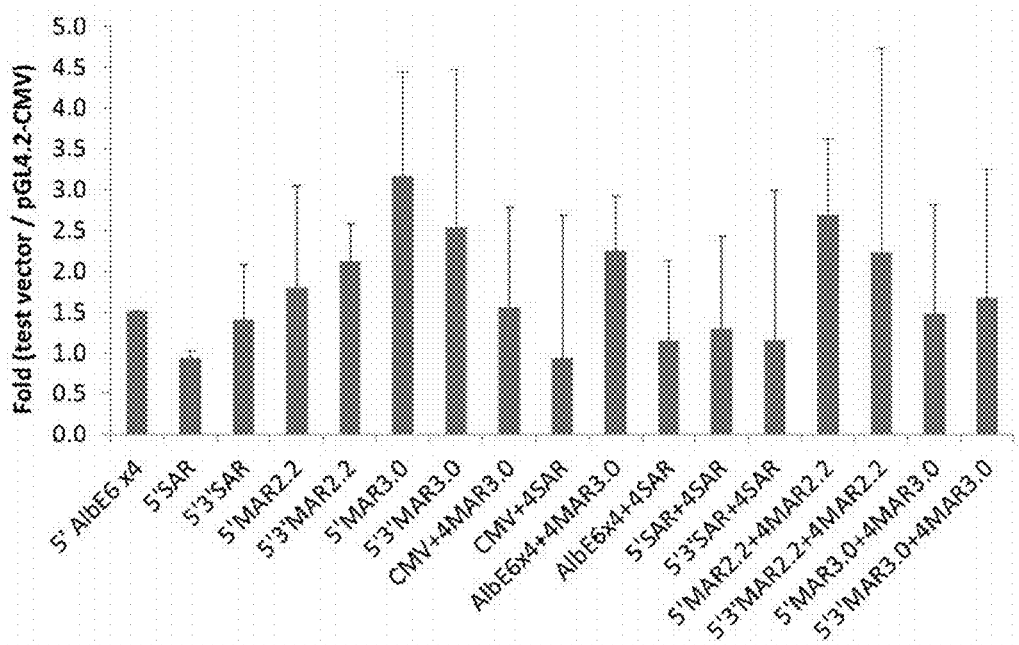
FIG. 2 shows the luciferase expression result of MAR candidate elements.

Firefly luciferase analysis method is as follows. First, the wells in which cells were being cultured were removed of the culture media, and washed by 1 mL each of 1×PBS. The transfected cells were added with Trypsin-EDTA at 100 μL/well, and allowed to react for 1 min at 37° C., to detach the cells from the bottom. Each well was added with 1 mL of culture medium. After counting the cell numbers, the transformed cells were dispensed into 1.5 mL tubes respectively after dilution to $1.0 \times 10^5$ cells/mL (based on viable cell counts) with culture medium. To a 96-well white plate, cells were placed in 100 μL/well for each tested DNA. The One-glo luciferase analysis reagent, which had been prepared in advance, was added to the wells in 100 μL/well, and allowed to react for 3 min at room temperature. Using a photometer (EG&G Berthold, Microplate luminometer LB 96V), the firefly RLU (relative light units) was measured. The measurement results regarding the test vectors as compared to pGL4.2-CMV are shown in FIG. 2 and Table 1.

As a result, 5' MAR element showed the best effect, which showed 1.6 to 5.3-fold increase in effect (average) as compared to pGL4.2-CMV control vector. Further, the differences in effects between the single and dual MARs or between Cis and Cis+Trans MARs were not found. As such, the test result values of the candidate elements showed no significant differences among them but showed great variations, and thus, the two elements, 5'MAR2.2 and 5'MAR3.0, were selected primarily.

TABLE 1

| Vector | Fold (Test Vector/pGL4.2-CMV) | | | | |
|---|---|---|---|---|---|
| | 1st | 2nd | 3rd | Ave. | S.D. |
| 5'Alb E6 x4 | 1.43 | 1.56 | 1.54 | 1.51 | 0.07 |
| 5'SAR | 1.71 | 0.45 | 0.67 | 0.94 | 0.68 |
| 5'3'SAR | 0.59 | 0.79 | 2.84 | 1.41 | 1.24 |
| 5'MAR2.2 | 1.30 | 2.10 | 2.01 | 1.80 | 0.44 |
| 5'3'MAR2.2 | 1.69 | 1.13 | 3.57 | 2.13 | 1.28 |
| 5'MAR3.0 | 2.64 | 1.55 | 5.31 | 3.17 | 1.93 |
| 5'3'MAR3.0 | 2.37 | 1.41 | 3.84 | 2.54 | 1.22 |
| CMV + 4MAR3.0 | 1.03 | 0.14 | 3.49 | 1.55 | 1.74 |
| CMV + 4SAR | 0.54 | 0.58 | 1.71 | 0.94 | 0.66 |
| Alb E6 x4 + 4MAR3.0 | 1.18 | 3.12 | 2.47 | 2.25 | 0.99 |
| Alb E6 x4 + 4SAR | 0.68 | 0.32 | 2.45 | 1.15 | 1.14 |
| 5'SAR + 4SAR | 0.40 | 0.07 | 3.41 | 1.29 | 1.84 |
| 5'3'SAR + 4SAR | 0.94 | 0.35 | 2.17 | 1.15 | 0.93 |
| 5'MAR2.2 + 4MAR2.2 | 2.41 | 0.33 | 5.32 | 2.69 | 2.51 |
| 5'3'MAR2.2 + 4MAR2.2 | 2.01 | 1.03 | 3.66 | 2.23 | 1.33 |
| 5'MAR3.0 + 4MAR3.0 | 1.10 | 0.14 | 3.21 | 1.48 | 1.57 |
| 5'3'MAR3.0 + 4MAR3.0 | 1.46 | 0.60 | 2.96 | 1.67 | 1.19 |

The effect of the MAR element was not good enough as expected, and thus the MAR effects regarding CMV and SV40 promoters were assessed. Specifically, PCR was conducted using pGL4.20 vector as a template and using the primer set of SEQ ID NOs: 9 and 10, to obtain DNA fragments containing an SV40 promoter. The DNA fragments amplified by PCR were purified by gel extraction and inserted into pCR2.1-TOPO plasmid vector. The presence of SV40 promoter represented by SEQ ID NO: 12 was verified through a cleavage mapping using restriction enzymes and DNA sequence analysis. And then pGL4.2-CMV, pGL4.2-CMV-5'MAR2.2 and pGL4.2-CMV-5'MAR3.0 vectors were treated with NheI and XhoI to remove the CMV promoter, and the SV40 promoter treated with the same restriction enzymes was inserted thereto, to prepare pGL4.2-SV40, pGL4.2-SV40-5'MAR2.2 and pGL4.2-SV40-5'MAR3.0 vectors.

Luciferase expression level in the adherent cell line CHO-K1 was measured by the same method as in MAR candidate element test. The stable cells were established through a selection period of about 2 weeks. The test was carried out in a total of 2 sets, and the firefly fluorescence values were measured in the same manner as described above.

Figure 3:
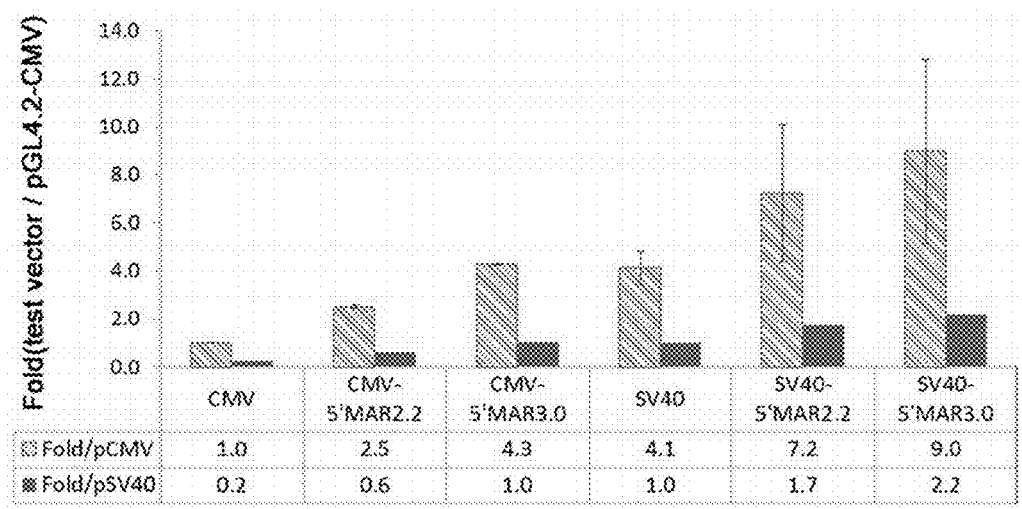
FIG. 3 shows the luciferase expression result of the comparative promoter test.

As shown in FIG. 3, SV40 showed about 4-fold increase in effect as compared to CMV promoter. Among them, pGL4.2-SV40-5'MAR3.0 vector showed the best result, which showed 9-fold and 2.2-fold gene expression-increasing effects as compared to CMV control group and SV40 control group, respectively.

1-2: LCR Element Selection

Figure 4:
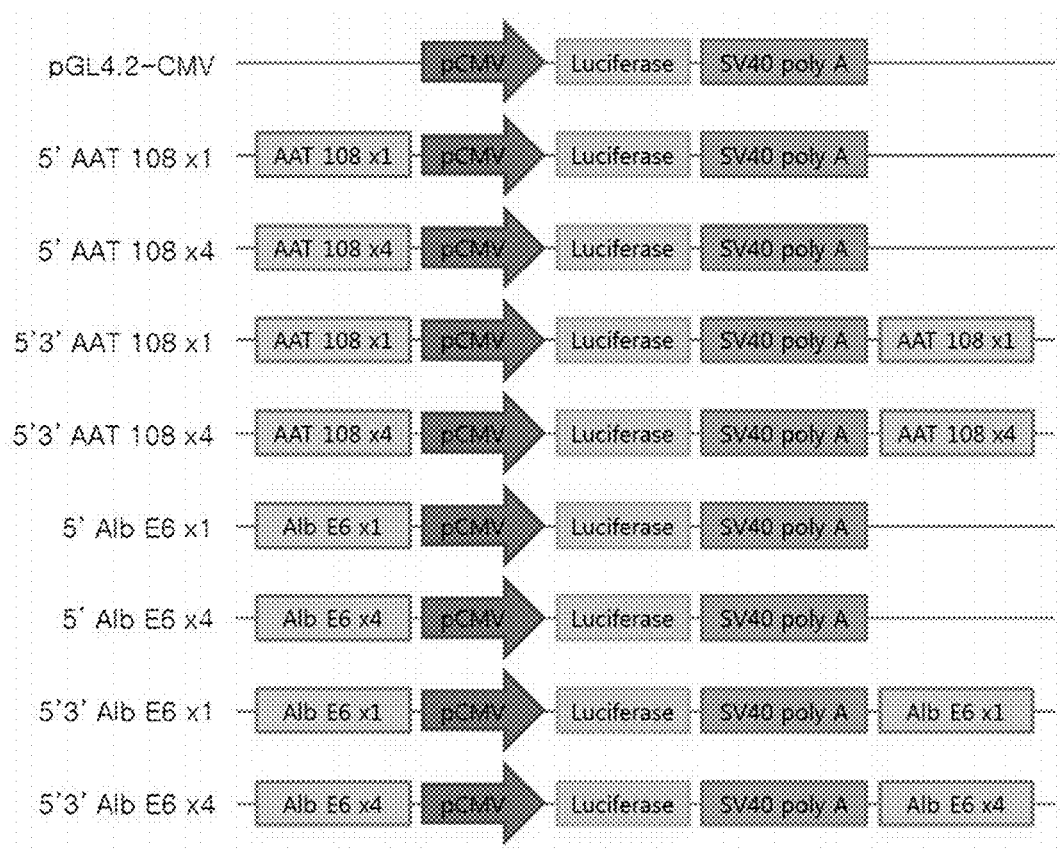
FIG. 4 shows a schematic diagram of luciferase vectors regarding LCR (locus control region) candidate elements.

Among the LCR elements disclosed in International Patent Publication No. WO 2009/102085, AAT 108 (α-1-antitrypsin precursor, 120 bp, SEQ ID NO: 13) and Alb E6 (serum albumin preproprotein, 81 bp, SEQ ID NO: 14), which showed Factor IX expression-increasing effects in vivo, were selected to evaluate the effects in vitro. AAT 108 or Alb E6 was added to the 5' region, the 3' region of the SV40 late poly (A) signal, and both the 5' and 3' regions of pGL4.2-CMV control vector to obtain various vectors for the test (See FIG. 4).

In addition, since the LCR elements are very short in length, the vectors in which 4 copies of the elements were multi-inserted into each site were prepared to assess the effect on the expression when the elements were multi-inserted.

Using the vectors (pCR-AAT108LCR, pCR-E6LCR) disclosed in International Patent Publication No. WO 2009-102085, the monomer of each element was obtained by conducting PCR one-time; and Alb E6×4 multimer was prepared by conducting the recombinant PCR for 4 times.

First, in order to obtain a monomer of each element, the primer set of SEQ ID NOs: 17 and 18 and the primer set of SEQ ID NOs: 19 and 20 were used for Alb E6×1 and AAT108×1, respectively. Then, the template was denatured at 94° C. for 2 min to separate DNA strands, and the DNA molecules were amplified by repeating a process of denaturing at 94° C. for 15 sec, annealing at 55° C. for 15 sec, and elongation at 72° C. for 1 min for 30 cycles, followed by additional elongation at 72° C. for 5 min. The DNA fragments amplified by PCR were purified by gel extraction and inserted into pCR2.1-TOPO plasmid vector. The presence of AAT108 and A1bE6 gene represented by SEQ ID NOs: 13 and 14, respectively, were verified through a cleavage mapping using restriction enzymes and DNA sequence analysis.

Figure 5:
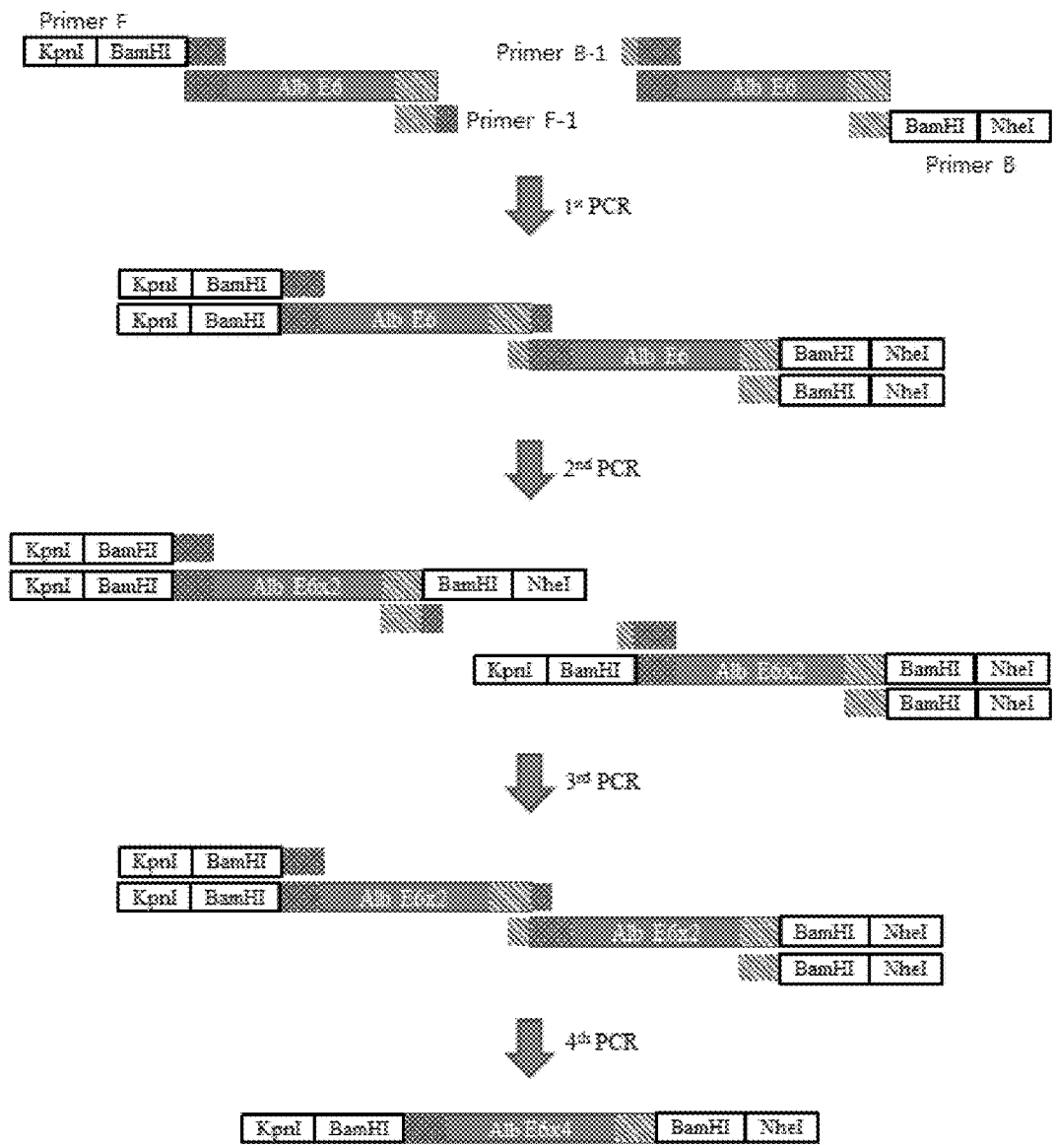
FIG. 5 shows a PCR strategy for preparing Alb E64×4 LCR element.

On the other hand, Alb E6×4 multimer was prepared by conducting the recombinant PCR for 4 times, as shown in FIG. 5. The PCR was conducted by the same method as above except that the annealing time was extended to 30 sec. Through a DNA sequence analysis, the presence of Alb E6×4 gene represented by SEQ ID NO: 16 was verified. AAT 108×4 multimer (SEQ ID NO: 15) was synthesized at Genscript Inc.

To insert an LCR element to the 5' region of the promoter in pGL4.2-CMV vector, vectors and the PCR product were cut with KpnI and NheI, followed by ligation. The cloned product was treated with the same restriction enzymes, and it was verified whether the band with a desired size was present on a DNA gel. Through the above procedure, 5'AAT 108×1, 5'AAT 108×4, 5'Alb E6×1, and 5'Alb E6×4 vectors were obtained.

In order to insert an LCR element to the 3' region of SV40 late poly(A) signal in pGL4.2-CMV vector, pGL4.2-CMV vector and Alb E6 element were cut with BamHI restriction enzyme and AAT 108 element was cut with BglII restriction enzyme. The resultants were inserted to pGL4.2-CMV vector using compatible ends. Through the above procedure, 3'AAT 108×1, 3'AAT 108×4, 3'Alb E6×1 and 3'Alb E6×4 vectors were obtained.

To insert LCR into the 5' region of the promoter and the 3' region of SV40 late poly(A) signal in pGL4.2-CMV vector, the vectors containing an LCR element at the 3' region of SV40 late poly(A) signal and the PCR product prepared above were cut with the restriction enzymes KpnI and NheI, followed by ligation. Through the above procedure, 5'3'AAT 108×1, 5'3'AAT 108×4, 5'3'Alb E6×1, and 5'3'Alb E6×4 vectors were obtained.

To assess the effect of the LCR element, CHO-K1 adherent cell line was subjected to transfection. 24 hrs prior to transfection, 500 µL each of CHO-K1 cell culture being subcultured in the DMEM (LONZA, 12-604F) (w/v 10% FBS) culture medium was dispensed into a 24-well plate at $0.5×10^5$ cells/well. 800 ng of test DNA (pGL4.2-CMV, 5'AAT 108×1, 5'AAT 108×4, 5'Alb E6×1, 5'Alb E6×4, 5'3'AAT 108×1, 5'3'AAT 108×4, 5'3'Alb E6×1, and 5'3'Alb E6×4, respectively) was mixed with Opti-MEM (Gibco, 31985-088) in a 1.5 mL tube to the total volume of 50 µL (based on 1 well). In other 1.5 mL tube, 2 µL of lipofectamine (Invitrogen, 11668027) was mixed with Opti-MEM to the total volume of 50 µL and allowed to react for 5 min at room temperature. The two solutions prepared above were mixed and allowed to react for 20 min at room temperature. The resultant was dispensed into the wells in 100 µL/well. 24 hrs later, the medium in each well was refreshed and 50 µg/mL puromycin (Gibco, A11138-03) as added to the wells for cell selection.

Regarding 7 sets, the stable cells were established through the selection period of about 2-4 weeks. Using the established stable cells, luciferase analysis was conducted by One-glo luciferase analysis system (Promega, E6110) by the same method as the MAR candidate element analysis. Among the results of 7 sets, the results of 3 sets which showed most similar results were chosen, and the effects of individual elements were compared. The firefly fluorescence value of each element was measured and corrected for the number of cells, which showed 0.54 to 3.94-fold increase as compared to pGL4.2-CMV vector (see FIG. 6).

Figure 6:
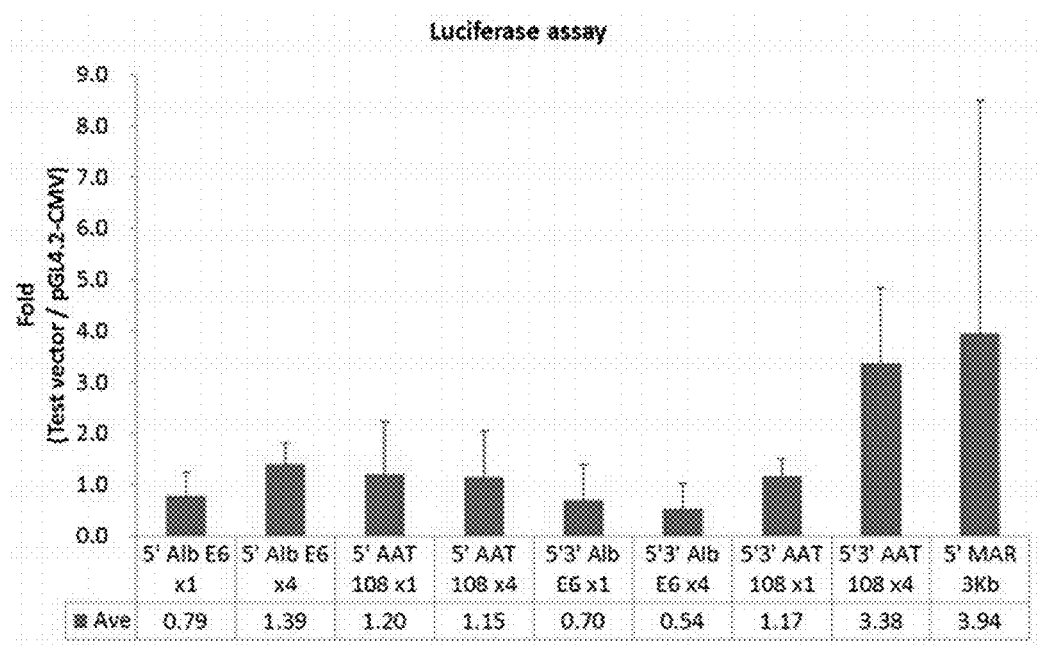
FIGS. 6 and 7 show the luciferase expression results of LCR candidate elements.

As shown in FIG. 6, the element which showed the best result was the conventionally used 5'MAR 3.0 kb element, which showed 0.24 to 9.02 (3.94±4.55)-fold increasing effect. Next, 5'3'AAT 108×4 element showed 1.79 to 4.67 (3.38±1.46)-fold increasing effect.

To assess the effects of pGL4.2-CMV-3'Alb E6, pGL4.2-CMV-3'Alb E6×4, pGL4.2-CMV-3'AAT 108×1 and pGL4.2-CMV-3'AAT 108×4 vectors in stable expression, the same tests as above were conducted. Puromycin selection was conducted for 2 weeks and 1 set of test was conducted. The result is shown in FIG. 7.

Figure 7:
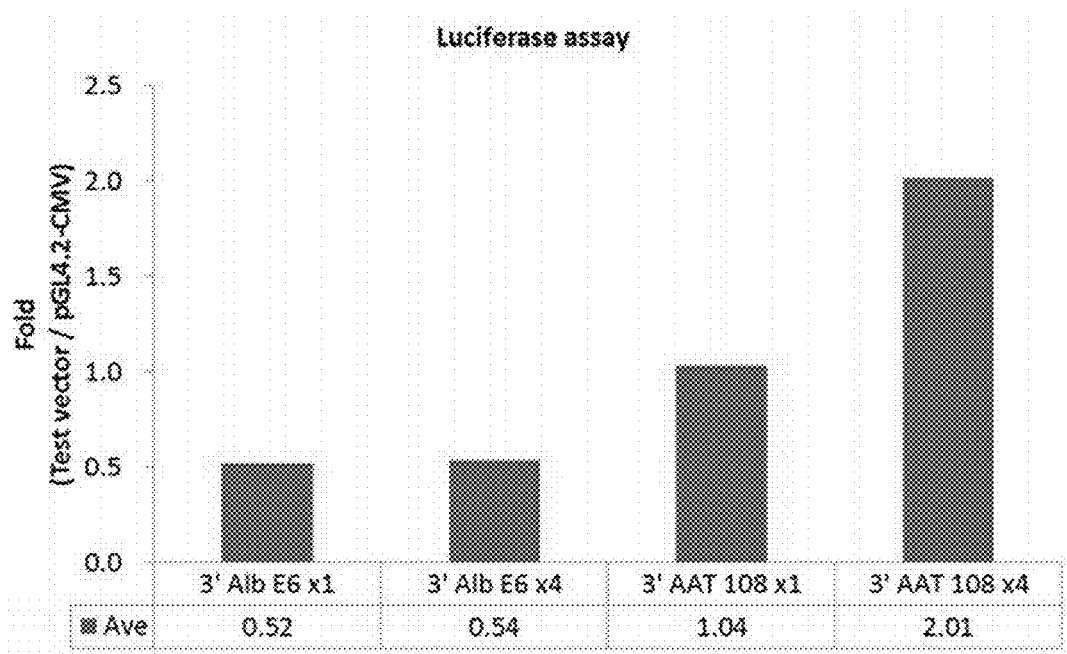

As shown in FIG. 7, pGL4.2-CMV-3'AAT 108×4 vector showed about 2-fold increase as compared to pGL4.2-CMV vector. It was considered that this result might explain although indirectly, that pGL4.2-CMV-5'AAT 108×4 vector showed no more than 1.15-fold average increase but pGL4.2-CMV-5'3'AAT 108×4 vector showed 3.38-fold average increase (see FIG. 6).

From results of the luciferase analysis test under the stable condition, 2 types of effective LCR elements were identified, but they did not show significant improvement as compared to the conventionally used 5'MAR 3.0 kb. Also, considering the big variations in the fluorescence measurement test, the vectors whose effects were verified in the present test, pGL4.2-CMV-3'AAT 108×4 vector and pGL4.2-CMV-5'3'AAT 108×4 vector, were chosen and it was planned that their expression levels of recombinant proteins would be assessed directly.

1-3: Intron Element Selection

To assess the effect of a chimeric intron by the expression of the deletion form of the human complement factor H (dCFH), the dCFH gene was prepared first.

Through 2 steps of PCR, dCFH having a total of 7 SCRs (short consensus repeats) was prepared by linking the SCRs #1~4 (Regulatory region) to SCRs #18~20 (Binding region), which were selected among 20 SCRs in the CFH, excluding 13 middle SCRs. In the test to be conducted as below, Phusion High-Fidelity DNA polymerase (Thermo/F-530S) was used as a polymerase; and the template was denatured at 98° C. for 30 sec to separate DNA strands, and the DNA molecules were amplified by repeating a process of denaturing at 98° C. for 10 sec, annealing at 55° C. for 30 sec, and elongation at 72° C. for 30 sec for 30 cycles, followed by additional elongation at 72° C. for 5 min.

SCR 1 F primer (SEQ ID NO: 21) contained the restriction enzyme NotI site, and SCR 20 B primer (SEQ ID NO: 24) contained the XhoI site, so that they may be used in the future cloning.

In the first step of PCR, the SCRs #1~5 were obtained using pMSGneo-hCFH as a template, and using SCR 1 F primer (SEQ ID NO: 21) and SCR 5(18) B primer (SEQ ID NO: 22) containing the back (3') region of SCR #5 and the front (5') region of SCR #18. Also, SCR fragments #18~20 were obtained using pMSGneo-hCFH as a template, and using SCR 18(5) F primer (SEQ ID NO: 23) containing the back (3') region of SCR #5 and the front (5') region of SCR #18 and SCR 20 B primer (SEQ ID NO: 24). The prepared two kinds of fragments were purified and recovered with Wizard® SV Gel and PCR Clean-Up system (Promega).

The preparation method of the above pMSGneo hCFH is as follows.

First, PCR was carried out using pCMV-SPORT6-hCFH vector (Imagene, #IRATp970B10140D) as a template, and using a primer pair (SEQ ID NOs: 47 and 48). PCR was carried out as follows: a total of 50 µL of PCR reaction mixture was prepared by mixing 5 ng of pCMV-SPORT6-hCFH, 1 µL of each primer (10 nmol/mL), 1 µL of PCR pre-mix (AccuPower® ProFi Taq PCR PreMix, Bioneer), and 46 µL of distilled water; and then the mixture was subjected to a reaction process of at 94° C. for 30 sec, at 65° C. for 60 sec, at 65° C. for 3 minute and 20 sec, for 30 cycles. After the PCR product was electrophoresed on 0.8% agarose gel, the gene fragments encoding hCFH were obtained by gel elution.

Then, the gene fragments encoding hCFH, and pMSGneo vector (Mogam Institute, Korea), a backbone vector, were treated with NotI and XhoI, respectively; then, they were ligated using T4 ligase to obtain an expression vector of hCFH; and the expression vector thus prepared was designated as "pMSGneo-hCFH".

Figure 8:
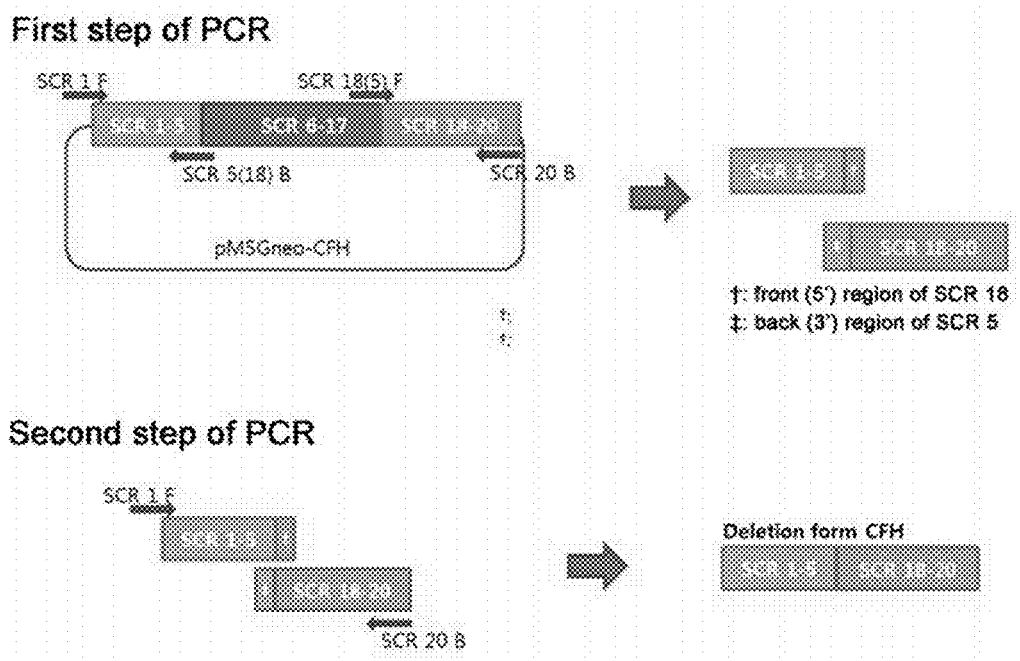
FIG. 8 shows the preparation process of dCFH (a deletion form of human complement factor H).

The second step of PCR was conducted using the 2 kinds of fragments obtained in the first step of PCR as templates, and using SCR 1 F primer (SEQ ID NO: 21) and the SCR 20 B primer (SEQ ID NO: 24). Using Phusion High-Fidelity DNA polymerase (Thermo/F-530S), the templates were denatured at 98° C. for 30 sec to separate DNA strands, and the DNA molecules were amplified by repeating a process of denaturing at 98° C. for 10 sec, annealing at 55° C. for 30 sec, and elongation at 72° C. for 45 sec for 30 cycles, followed by additional elongation at 72° C. for 5 min, to obtain dCFH gene (SEQ ID NO: 46) (FIG. 8).

Next, the expression vector pcDNA-dCFH was prepared.

The pMSGneo-dCFH vector and pcDNA3.1(+) vector were cut with NotI and XhoI restriction enzymes for about 3 hr at 37° C. The cut vectors were electrophoresed on the agarose gel; and the dCFH genes among the cut pMSGneo-dCFH genes, and the gene with a size of the vector among the cut pcDNA3.1(+) genes were excised from the gel. The excised genes were purified and recovered with Wizard® SV Gel and PCR Clean-Up system. The cut genes were reacted at 16° C. for about 6 hrs using the DNA Ligation Kit Ver. 2.1, to prepare pcDNA-dCFH expression vector.

Then, pcDS-dCFH expression vector was prepared. The pcDNA3.1(+) vector and Y11 LC pcIW vector (See: *Nucleic Acids Res.*, 2008 September; 36(15):e96) were cut with NheI (NEB/R0131S) and NotI restriction enzymes. The cut genes were electrophoresed on the agarose gel; and the chimeric intron genes (SEQ ID NO: 25) among the cut Y11 LC pcIW vector genes, and the cut pcDNA3.1(+) vector gene were excised from the gel. The excised genes were purified and recovered with Wizard® SV Gel and PCR Clean-Up system. The cut genes were reacted at 16° C. for about 6 hrs using the DNA Ligation Kit Ver. 2.1, to prepare pcDS-MCS vector. Further, using the pcDS-MCS vector and pcDNA-dCFH vector prepared above, pcDS-dDFH vector was prepared through the method as above, in which dCFH gene was inserted into the NheI/NotI cleavage site of pcDS-MCS vector.

To secure WPRE gene (SEQ ID NO: 26), PCR was conducted using Y11 LC pcIW vector as a template. In the test to be conducted as below, Phusion High-Fidelity DNA polymerase (Thermo/F-530S) was used as a polymerase; and the template was denatured at 98° C. for 30 sec to separate DNA strands, and the DNA molecules were amplified by repeating a process of denaturing at 98° C. for 10 sec, annealing at 55° C. for 30 sec, and elongation at 72° C. for 30 sec for 30 cycles, followed by additional elongation at 72° C. for 5 min. The WPRE F primer used herein (SEQ ID NO: 27) contained the restriction enzyme XhoI site, and the WPRE B primer (SEQ ID NO: 28) contained the XbaI site, so that they may be used in the future cloning. The obtained PCR products were purified and recovered with Wizard® SV Gel and PCR Clean-Up system.

The WPRE gene obtained by the above PCR and pcDS-dCFH vector were cut with XhoI and XbaI (NEB/R0145S) restriction enzymes at 37° C. for about 1 hr. The cut genes were purified and recovered with Wizard® SV Gel and PCR Clean-Up system. The cut genes were reacted at 16° C. for about 3 hrs using the DNA Ligation Kit Ver. 2.1, to prepare pcDSW-dCFH vector, in which WPRE gene was inserted into the XhoI/XbaI cleavage site of pcDS-dCFH vector.

Figure 9:
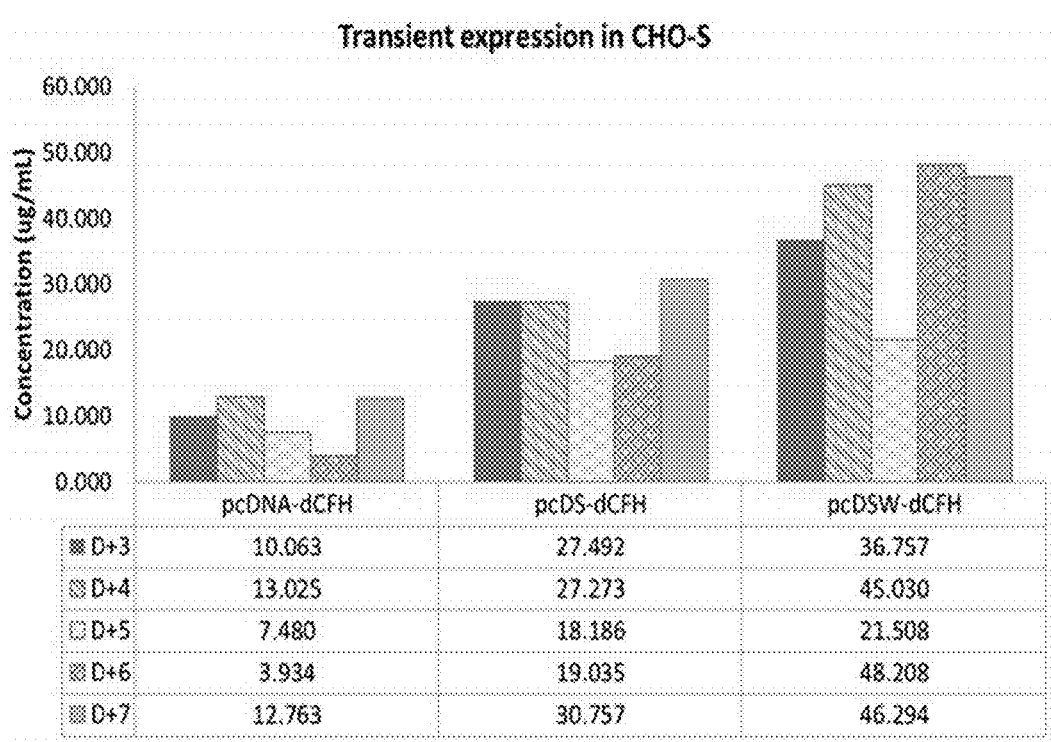
FIG. 9 shows the expression levels of dCFH in CHO—S cells.

In order to verify the transient expression level-increasing effect of the chimeric intron, CHO—S cell (Invitrogen, #R800-07) was prepared. The cells were thawed; seeded into 30 mL of FreeStyle CHO expression medium (Invitrogen, #12651-014) in 3×10$^5$ cells/mL using Erlenmeyer scale; and kept for 2~3 passages so that they could grow up to 1.2~2.0×10$^6$ cells/mL in 2~3 days. Then, the cells were transfected with pcDNA-dCFH vector, pcDS-dCFH vector and pcDSW-dCFH vector prepared above using Freestyle™ Max reagent (Invitrogen, #16447-100). After the transfection, 1 mL of the culture solution was collected once a day from day 3 to day 7. Using the collected culture solutions, the number of cells and viability were measured; and using the human complement factor H ELISA kit (Hycult biotech, #HK342), the dCFH expression levels were verified (FIG. 9).

The CHO—S cells transfected with pcDNA-dCFH vector showed the maximum expression level of about 13.025 μg/mL, whereas the CHO—S cells transfected with pcDS-dCFH vector and pcDSW-dCFH vector showed the maximum expression levels of about 30.757 μg/mL and 48.208 μg/mL, respectively. Each vector showed about 2.4 to 3.7 times higher expression level than pcDNA-dCFH.

Second, in order to verify the effect of a chimeric intron, the prepared dCFH expression vector was transfected into FreeStyle™ 293-F cell (Invitrogen/R790-07). FreeStyle™ 293-F cell was cultured in Freestyle 293 expression medium (Gibco/12338-018). 24 hr prior to the transfection, the cells were passaged at 7×10$^5$ cells/mL.

On the day of transfection, the cells were diluted in a 125 mL Erlenmeyer flask using culture medium to the total volume of 30 mL at 7×10$^6$ cells/mL In a 1.5 mL tube, 30 μg of plasmids for transfection (pcDNA-dCFH, pcDS-dCFH and pcDSW-dCFH) and OptiPRO™ SFM (Gibco/12309-019) were mixed to the total volume of 600 μL. In a new 1.5 mL tube, 90 μL of PEI MAX (Polyscience/24765-2) (1 μg/μL) and 510 μL of OptiPRO™ SFM were mixed. The solution containing plasmids and the solution containing PEI MAX were mixed and reacted for 10 min at room temperature. While the Erlenmeyer flask containing 293-F cell was slowly turned around, the mixed solution was added thereto. The cells were cultured in a 5% CO$_2$ suspension incubator at 37° C. with 130 rpm for 7 days. The culture medium was collected in a 1.5 mL tube for 7 day from day 3, and centrifuged for 3 min at 5000 rpm to precipitate the cells. Then, the supernatant was taken and using the human complement facter H ELISA kit (Hycult biotech/HK342), dCFH expression level was measured (FIG. 10).

Figure 10:
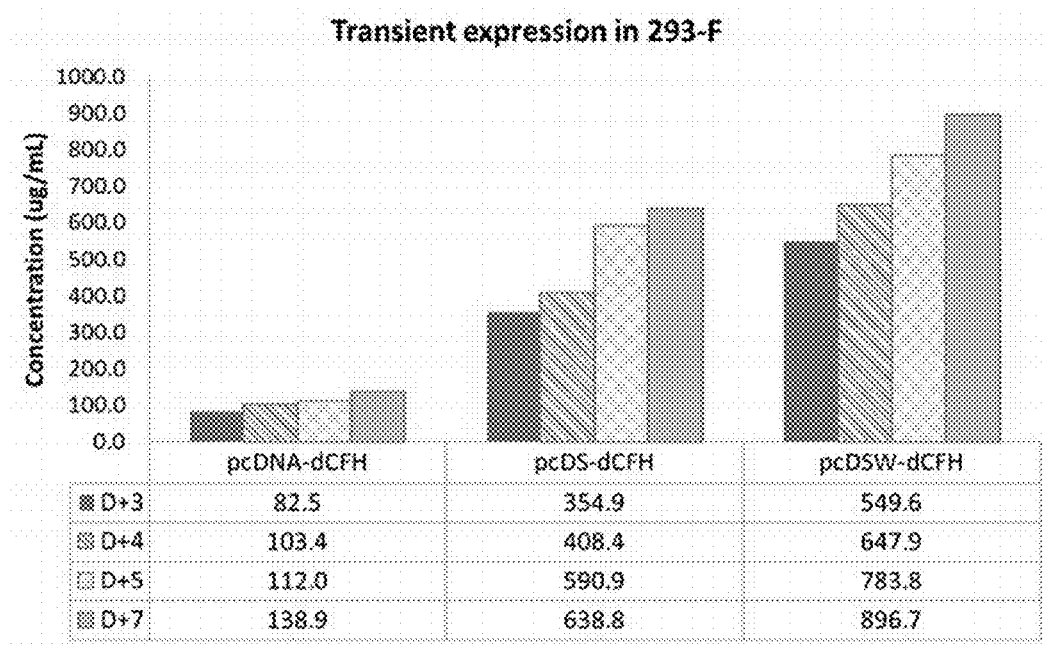
FIG. 10 shows the expression levels of dCFH in 293-F cells.

As shown in FIG. 10, the cells transfected with pcDNA-dCFH, pcDS-dCFH and pcDSW-dCFH showed the maximum expression levels of about 138.9 μg/mL, 638.8 μg/mL and 896.7 μg/mL, respectively. The cells transfected with the vectors containing a chimeric intron showed about 4.6-fold increase, and the cells transfected with the vectors containing both the chimeric intron and WPRE showed about 6.5-fold increase, as compared to pcDNA-dCFH expression vector.

Lastly, in order to verify the effect on the stable expression of a chimeric intron, CHO-DG44 cell (DR L. Chasin, Columbia University) was prepared. The cells were thawed; seeded into the MEM a w/HT (Gibco, 12571-063)+10% DFBS (Biotechnics research, 7103) medium at 3×10$^6$ cells/T75 flask; and kept for 2~3 passages so that they could grow up to the confluency of 90% in 2~3 days. Then, the prepared pcDNA-dCFH vector, pcDS-dCFH vector and pcDSW-dCFH vector were transfected into the cells using lipofectamine® 2000 transformation reagent (Invitrogen, #11668-027) at 5×10$^6$ cells/flask. 48 hrs after the transfection, the medium was replaced with a medium supplemented with 500 μg/mL of G418 for the cell selection. While monitoring the cell growth for about a week, the first passage was carried out at 80~90% confluency. If the cells showed about 80~90% confluency in 2~3 days after the first passaging, two more passages were carried out, and the cells were inoculated into a T75 flask at $5 \times 10^6$ cells/flask in the same manner, and then 1 mL of the culture solution was collected once a day from day 3 to day 7. On the last day of day 7, the number of cells and viability were counted after treating the cells with 0.25% trypsin-EDTA (Invirtogen, #25200-056); and the dCFH expression level was measured using the human complement factor H ELISA kit (Hycult biotech, # HK342) (FIG. 11).

Figure 11:
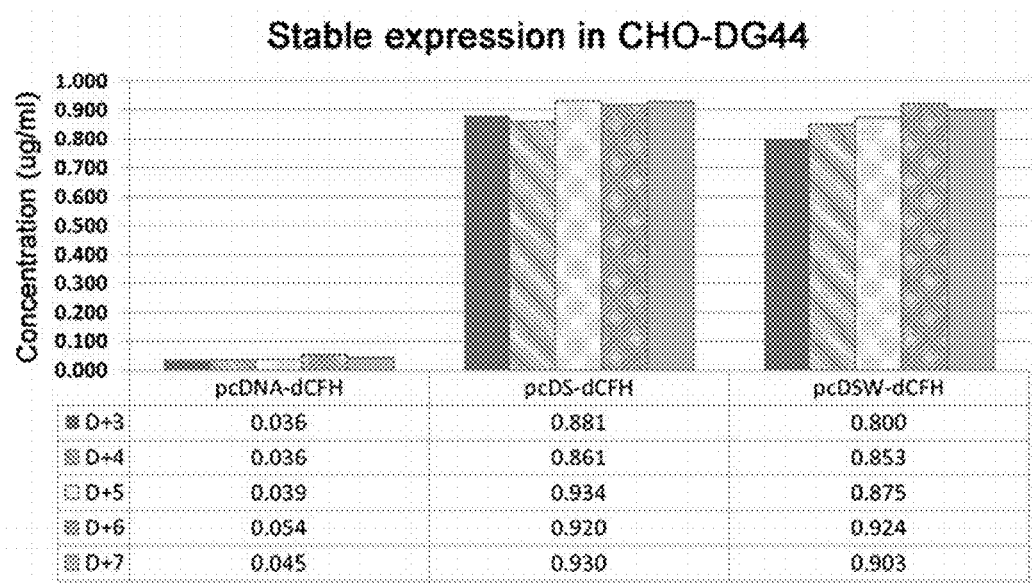
FIG. 11 shows the expression levels of dCFH in CHO-DG44 stable cells.

As shown in FIG. 11, CHO-DG44 cells transfected with pcDNA-dCFH vector showed the maximum expression level of about 0.054 μg/mL, whereas CHO-DG44 cells transfected with pcDS-dCFH vector and pcDSW-dCFH vector showed the maximum expression levels of about 0.934 μg/mL and 0.924 μg/mL, respectively. Each vector showed about 17.3 to 17.1 times higher expression level than pcDNA-dCFH.

1-4: Selection of Additional Elements

Additional selection was carried out by comparing the levels of FIX (Factor IX) protein expression using the four elements which were selected at the primary selection of MAR and LCR elements. It was planned that vectors would be prepared by removing luciferase gene from the luciferase vector prepared above and inserting FIX gene thereto. For use in the novel vector preparations, a primer set (SEQ ID NOs: 29 and 30) was prepared such that the primers include XhoI, PacI and ApaI restriction enzyme sites at the front, and ApaI and FseI sties at the back of the FIX gene.

Then, PCR was carried out using pMSG-FIX vector, as a template, and the primer set (SEQ ID NOs: 29 and 30).

The preparation method of the pMSG-FIX vector is as follows. First, mRNA was extracted from human liver cells using oligo-dT column (Invitrogen, USA) for the separation of FIX gene. After preparing a primer set (SEQ ID NOs: 49 and 50) which binds with the FIX gene-specific 5' end and 3' flanking region based on the FIX gene sequence registered in the gene bank (Ref.; Genbank accession No. M11309; 1~2775 bp), RT-PCR was carried out using the Titan one tube RT-PCR system (Roche) to synthesize FIX cDNA with the size of about 1,383 bp (461 amino acids), which was then cloned into pGEM-T vector (Promega).

The separated FIX gene was amplified by PCR using a primer set (SEQ ID NOs: 51 and 52) including NheI and BglII, and cloned into pMSG vector (Mogam Biotechnology institute, Korea), which is animal cell expression vector. FIX gene obtained from the PCR was cleaved using Nhe I and BglII restriction enzymes (New England Bio Labs, USA), and then subjected to 1.2% agarose gel electrophoresis to separate the gene with the size of 1.4 kb. The separated FIX gene was ligated to pMSG vector which was pre-treated with NheI and BglII restriction enzymes, to prepare FIX expression vector. *E. coli* DH5a was transformed with the DNA mixture, in which ligation reactions were completed, using $CaCl_2$ precipitation. The transformed *E. coli* was spread on an LB plate containing 50 μg/mL ampicillin, and cultured over night at 37° C. After culturing the colonies formed on the culture plate, plasmids were isolated using QIA filter mini-Plasmid Kit (Qiagen, Germany). The isolated plasmid DNA was confirmed to contain the FIX DNA fragments by the treatment with NheI/BglII restriction enzymes. The expression vector thus prepared was designated as "pMSG-FIX".

Figure 12:
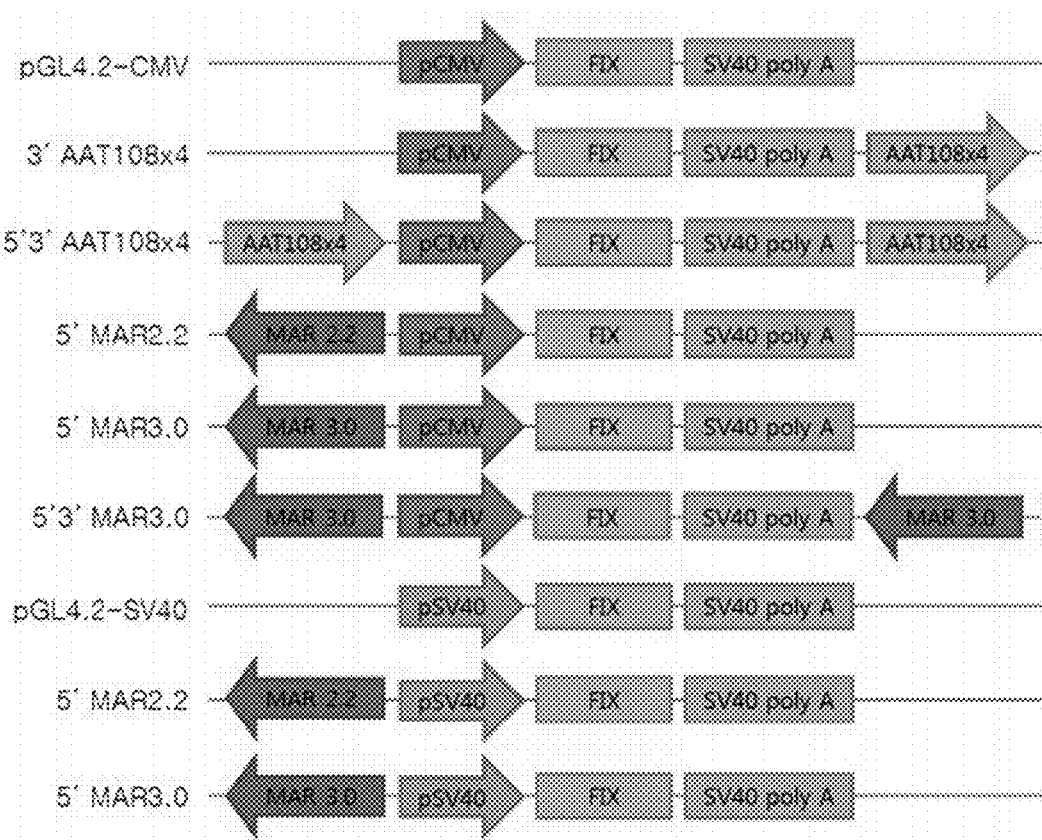
FIGS. 12 and 13 show a schematic diagram of FIX expression vector set 1 and its expression result, respectively.

The DNA fragments amplified by PCR were purified by gel extraction and inserted into pCR2.1-TOPO plasmid vector. The presence of FIX gene represented by SEQ ID NO: 31 was verified through a cleavage mapping using restriction enzymes and DNA sequence analysis. To the vector in which luciferase gene was removed using XhoI and FseI restriction enzymes, FIX gene was inserted using the same restriction enzymes. The schematic picture of the FIX expression vector set 1 thus prepared is shown in FIG. 12.

FIX expression in the adherent cell line CHO-K1 was measured by the same method as luciferase expression test. In the same manner as described above, stable cells were established through a selection period of about 2 weeks. The test was carried out in a total of 4 sets, and the FIX expression level was measured by ELISA method and corrected for the number of cells.

FIX ELISA method is as follows. Culture media in the wells were collected to 1.5 mL tubes. Each well was washed with 1 mL of 1×PBS. 100 μL/well of trypsin-EDTA was added to the wells, which were then allowed to react in a cell incubator at 37° C. for one minute to detach the transfected cells from the bottom. Each well was added with 1 mL of culture medium to collect cells, and the number of cells was counted. In the case of continuous cultures, the cells were cultured with passages at $0.5{\sim}1.0 \times 10^5$ cells/mL using 12-well plates, and cell selection was carried out using puromycin (50 μg/mL).

The capture antibodies provided by the Matched-pair Antibody set for ELISA of human Factor IX antigen (Affinity Biological, FIX-EIA) were diluted to 1/100 using a coating buffer (50 mM carbonate buffer; pH adjusted to 9.6 after adding 1.59 g of $Na_2CO_3$ and 2.93 g of $NaHCO_3$ to 1 L of tertiary distilled water). The diluted capture antibodies were dispensed into a 96-well ELISA plate at 100 μL/well, and allowed to react for 2 hrs at room temperature. The wells were washed 3 times with PBS-Tween buffer. Then Factor FIX (Benefix, 250 μg/mL) as a standard was prepared through 1/2 stepwise dilutions from 50 ng/mL to 0.781 ng/mL using a dilution buffer. The culture medium collected first was diluted to 1/10, 1/100 and 1/1000 using a dilution buffer (1% BSA in 1×PBS), and then added to the wells at 100 μL/well and allowed to react for 1 hr and 30 min at room temperature. The wells were washed 3 times with PBS-Tween buffer. Each well was added with 100 μL of TMB microwell peroxidase substrate, and allowed to react for 10 min at room temperature. Each well was then added with 100 μL of 2.5M $H_2SO_4$ to stop the reaction, and absorbance was read using a microplate reader at 450 nm.

Figure 13:
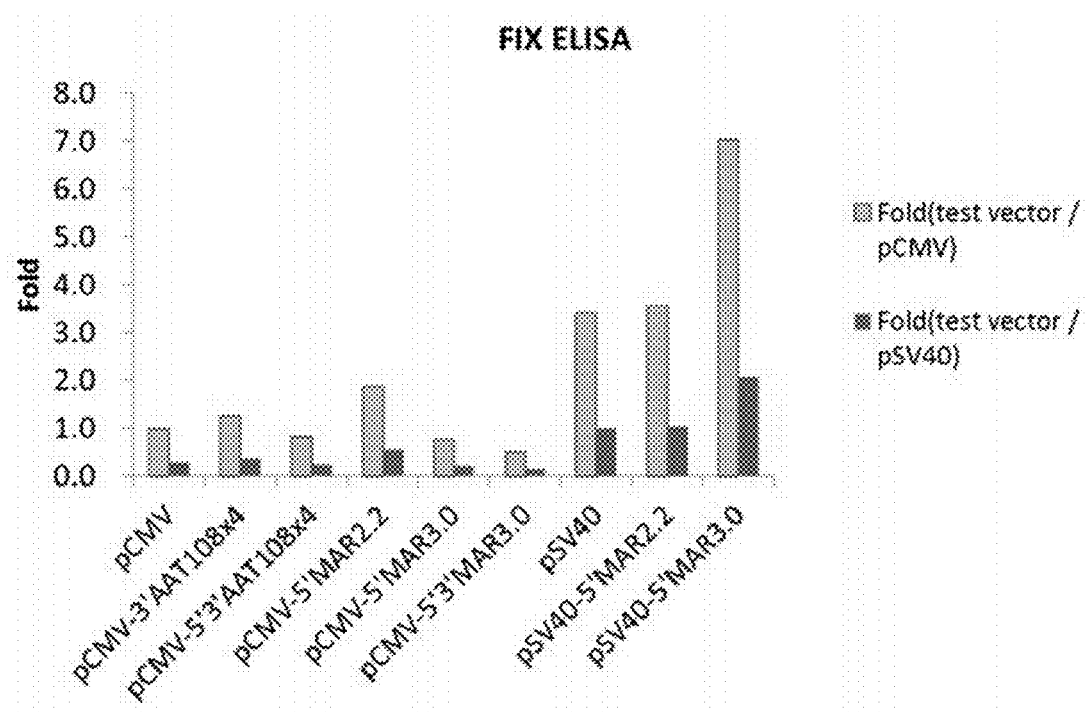

As shown in FIG. 13 and Table 2 below, the overall tendency was similar to the previous results with the luciferase. The SV40 promoter showed about 3.4 times higher increasing effect as compared to CMV promoter. The most effective was pGL4.2-SV40-5'MAR3.0 vector, which showed 7-fold and 2.1-fold expression level-increasing effect as compared to the CMV control group and SV40 control group, respectively.

TABLE 2

| Vector | Fold (Test Vector/pCMV-FIX) | | | | | | | | | |
|---|---|---|---|---|---|---|---|---|---|---|
| | #1 | | #2 | | #3 | | #4 | | | |
| | 1st | 2nd | 1st | 2nd | 1st | 2nd | 1st | 2nd | Ave. | S.D. |
| pCMV | 1.00 | 1.00 | 1.00 | 1.00 | 1.00 | 1.00 | 1.00 | 1.00 | 1.00 | 0 |
| pCMV-3'AAT108×4 | 1.67 | 1.86 | 0.58 | 0.25 | 2.19 | 3.24 | 3.10 | 5.27 | 1.26 | 1.61 |
| pCMV-5'3'AAT108×4 | 0.78 | 0.50 | 0.65 | 0.46 | 1.73 | 1.13 | 2.76 | 6.66 | 0.81 | 2.1 |
| pCMV-5'MAR2.2 | 0.47 | 0.23 | 2.26 | 3.89 | 1.24 | 0.89 | 2.79 | 3.30 | 1.87 | 1.37 |
| pCMV-5'MAR3.0 | 0.89 | 0.80 | 0.51 | 0.41 | 1.69 | 1.28 | 1.58 | 2.00 | 0.74 | 0.58 |
| pCMV-5'3'MAR3.0 | 0.87 | 0.27 | 0.29 | 0.23 | 0.91 | 1.25 | 1.60 | 2.48 | 0.50 | 0.78 |
| pSV40 | 3.58 | 3.27 | 1.95 | 2.42 | 7.44 | 12.07 | 7.44 | 8.81 | 3.42 | 3.61 |
| pSV40-5'MAR2.2 | 4.21 | 2.69 | 2.14 | 1.74 | 8.86 | 10.88 | 9.67 | 20.82 | 3.56 | 6.45 |
| pSV40-5'MAR3.0 | 5.97 | 5.07 | 5.62 | 6.47 | 13.11 | 12.51 | 18.54 | 27.96 | 7.05 | 8.06 |

Figure 14:
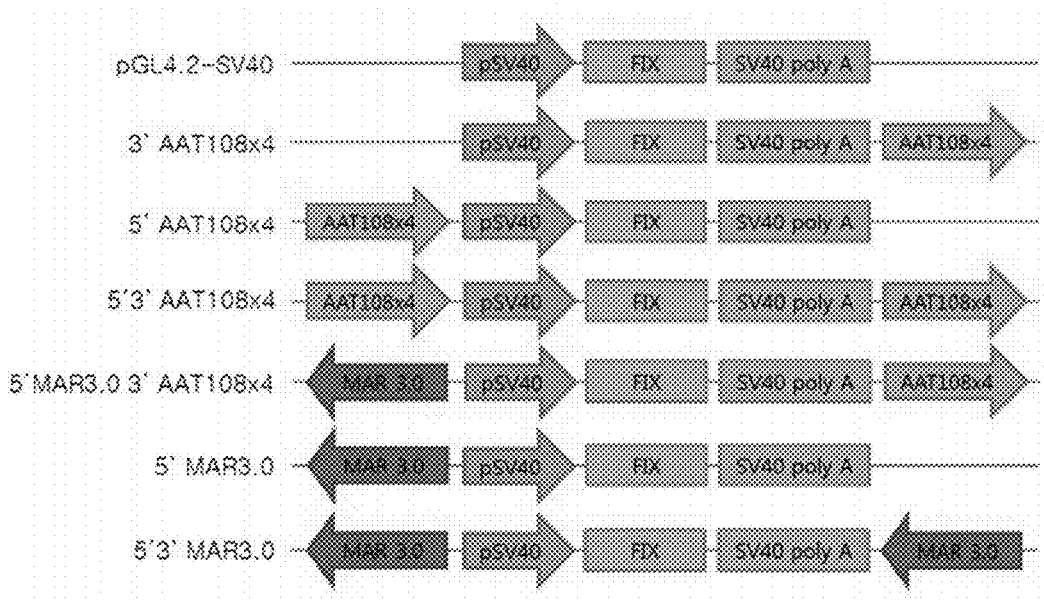
FIGS. 14 and 15 show a schematic diagram of FIX expression vector set 2 and its expression result, respectively.

In order to examine the effects of the LCR elements under the control of the SV40 promoter, the vectors were subjected to a cloning process for promoter replacement. The CMV promoter was removed from the above-prepared vectors having CMV promoter using NheI and XhoI restriction enzymes, and SV40 promoter was inserted using the same restriction enzymes. Additionally, vectors having the combination of 5'MAR and 3'AAT108×4, and 5'3'MAR3.0 vectors were prepared and used in the test. The schematic picture of the prepared FIX expression vector set 2 is illustrated in FIG. 14.

FIX expression in the adherent cell line CHO-K1 was measured by the same method as for FIX expression vector set 1. The stable cells were established through a selection period of about 2 weeks. The test was carried out in a total of 3 sets, and the FIX expression level was measured by ELISA method and corrected for the number of cells.

Figure 15:
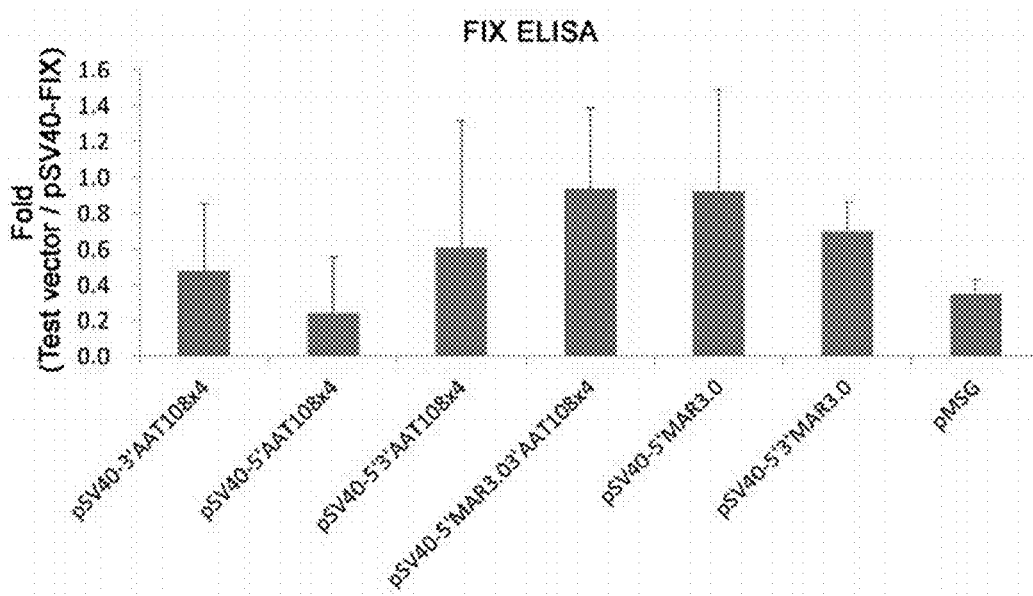

As shown in FIG. 15 and Table 3 below, there were no cases which showed increase in the expression level as compared to SV40 control group; and in the LCR candidate group with a replaced SV40 promoter, no vector showed higher expression level as compared to pSV40-5'MAR3.0. As such, through the comparison of the FIX expression levels, SV40 promoter and 5'MAR3.0 element were selected.

TABLE 3

| Vector | Fold (Test Vector/pSV40-FIX) | | | | |
|---|---|---|---|---|---|
| | #1 | #2 | #3 | Ave. | S.D. |
| pSV40 | 1.00 | 1.00 | 1.00 | 1.00 | 0.00 |
| pSV40-3'AAT108×4 | 0.23 | 0.82 | 0.60 | 0.49 | 0.30 |
| pSV40-5'AAT108×4 | 0.04 | 0.38 | 0.66 | 0.27 | 0.31 |
| pSV40-5'3'AAT108×4 | 0.35 | 0.39 | 1.55 | 0.60 | 0.68 |
| pSV40-5'MAR3.03'AAT108×4 | 0.70 | 1.38 | 0.98 | 0.97 | 0.34 |
| pSV40-5'MAR3.0 | 0.65 | 1.52 | 0.78 | 0.95 | 0.47 |
| pSV40-5'3'MAR3.0 | 0.67 | 0.80 | 0.84 | 0.74 | 0.09 |
| pMSG | — | 0.28 | 0.41 | 0.28 | 0.09 |

Example 2: Preparation of the Novel Vectors

The novel vectors were prepared using the elements selected in Example 1. The pSV40-5'MAR3.0-FIX vector used in the FIX expression comparison test was treated with ApaI restriction enzyme to remove FIX gene, and allowed to self-ligate, to obtain pSV40-5'MAR3.0-MCS vector. The MCS included 4 types of restriction enzyme sites: XhoI, PacI, ApaI and FseI.

Figure 16:
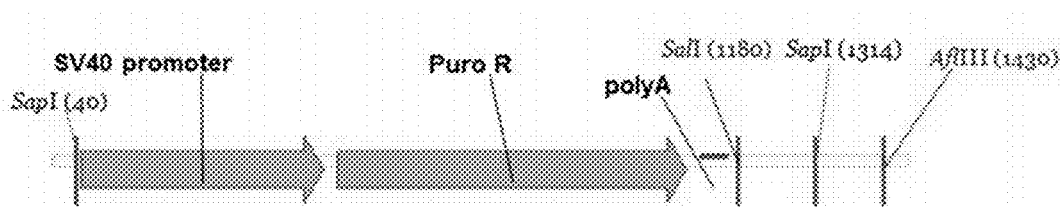
FIG. 16 shows a restriction enzyme map of puromycin expression system.

Puromycin selection region in the pSV40-5'MAR3.0-MCS vector was replaced with DHFR expression region to additionally prepare a vector having DHFR gene. Upon examining the restriction enzyme sites for the replacement, it was found that two SapI sites were present (at the front and the back); and the SapI site at the back was removed by treating with San and AflIII and preparing blunt ends using Klenow enzyme followed by self-ligation. A schematic picture of the restriction enzyme map of the puromycin expression system (pMS-P-MCS) is shown in FIG. 16.

As the required DHFR expression system, that of pDCH1P vector, which had been conventionally used in the present institute, was used. In about 2.5 kb including Hamster DHFR gene, 5' flank and 3' flank, promoter and polyA portion were confirmed based on the references (*Proc Natl Acad Sci.*, 1991, vol 88. p 8572; and *Mol. Cell. Biol.*, 1984, Vol. 4, p 38), and PCR primers (SEQ ID NOs: 32 and 33) were designed for reducing the size to about 1.5 kb.

Figure 17:
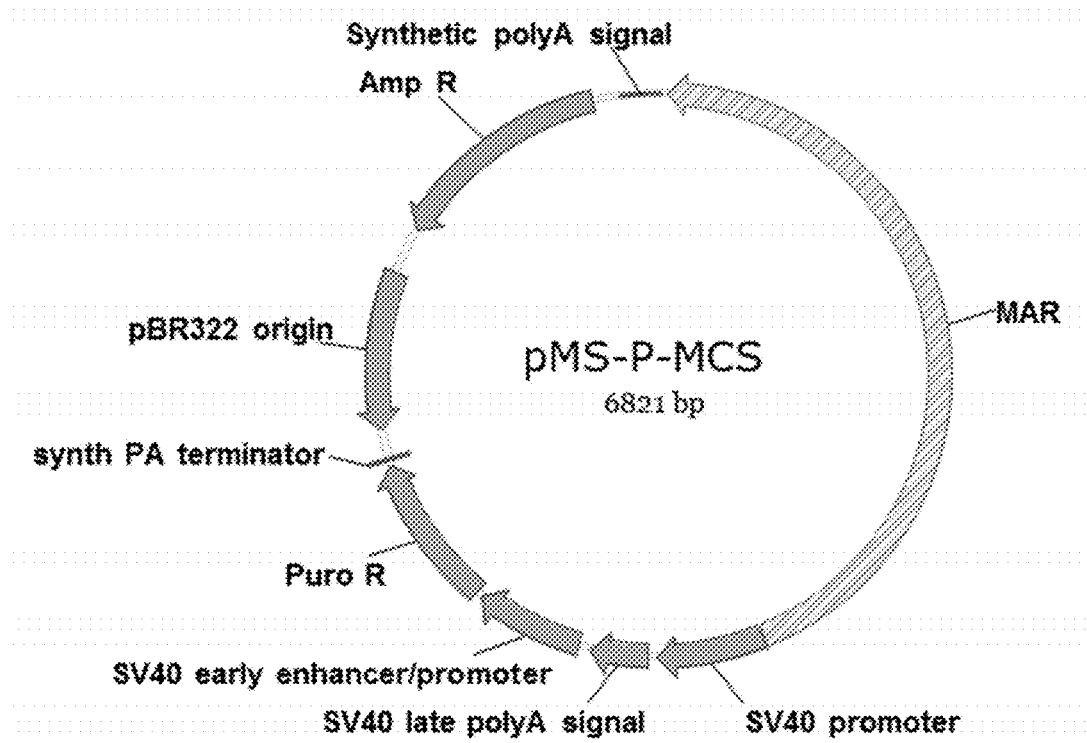
FIG. 17 shows the structures of a pair of novel vectors, pMS-P-MCS and pMS-D-MC.
Figure 17:
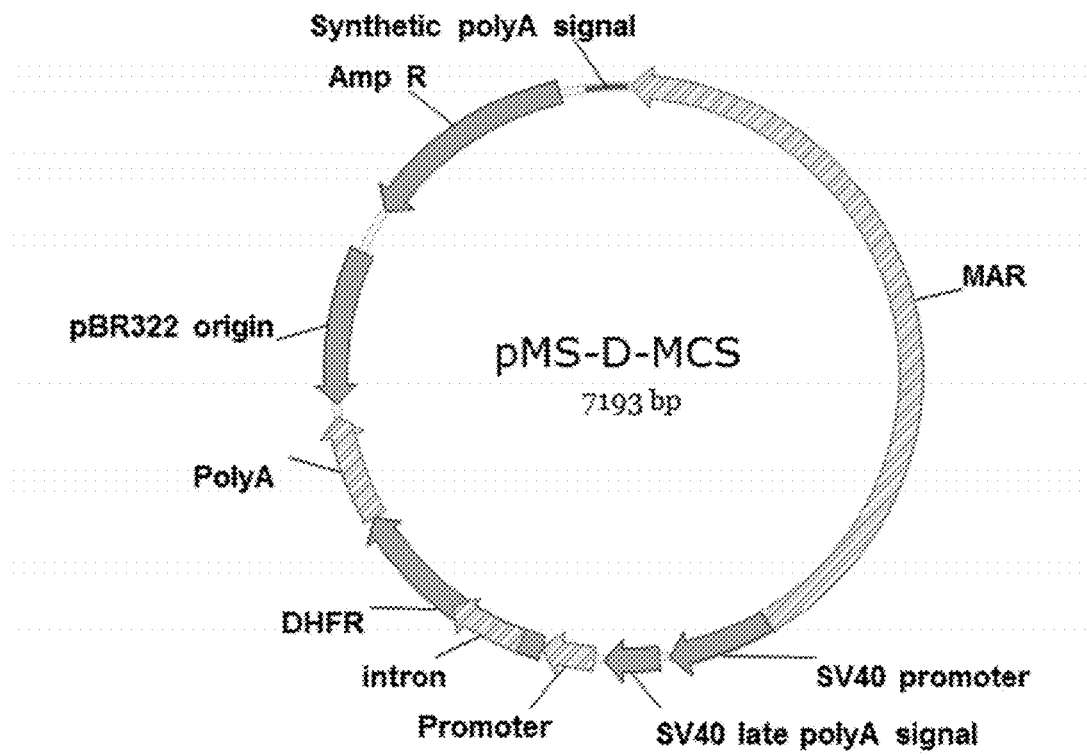

PCR was carried out using pDCH1P vector as a template to obtain a DNA fragment, which was then inserted into pCR2.1-TOPO vector, and sequenced (SEQ ID NO: 34). The DHFR expression region whose gene sequence had been verified was inserted into pSV40-5'MAR 3.0-MCS vector. Vectors and inserts were each cut with SapI and San restriction enzymes, and were connected again. The cloned product was treated with the same restriction enzymes, and it was verified whether the band with a desired size was present on the DNA gel. Through the above procedure, a novel vector pair I (pMS-P-MCS and pMS-D-MCS) was prepared (FIG. 17).

In order to compare the gene expression abilities of the prepared pair of novel vectors with the conventional vectors, ER2 antibody (EGFR antibody; see Korea Patent No. 1108642) gene was cloned into each of the pair of novel vectors and the pMSGneo vector (Mogam Biotechnology Institute, Korea) which is a conventional MAR vector. For the cloning into two kinds of vectors, both light and heavy chains of ER2 antibody were added with XhoI and NheI sites at the 5' region, and PacI and XhoI sites at the 3' region, and then PCR was carried out. For the PCR, pOptiVEC-ER2HC and pcDNA3.3-ER2LC vectors were each used as a template, and the HC (SEQ ID NOs: 35 and 36) set and the LC (SEQ ID NOs: 37 and 38) set were used as the primers for the heavy chain and the light chain, respectively. The PCR product was inserted into pCR2.1-TOPO vector, and DNA sequence (SEQ ID NOs: 42 and 43) was confirmed.

Light chain and heavy chain genes of the ER2 antibody whose sequences had been verified were cloned into pMS- Gneo vector using NheI and XhoI restriction enzymes, and were also cloned respectively into the pair of novel vectors (pMS-P-MCS and pMS-D-MCS) using XhoI and PacI restriction enzymes.

Figure 18A:
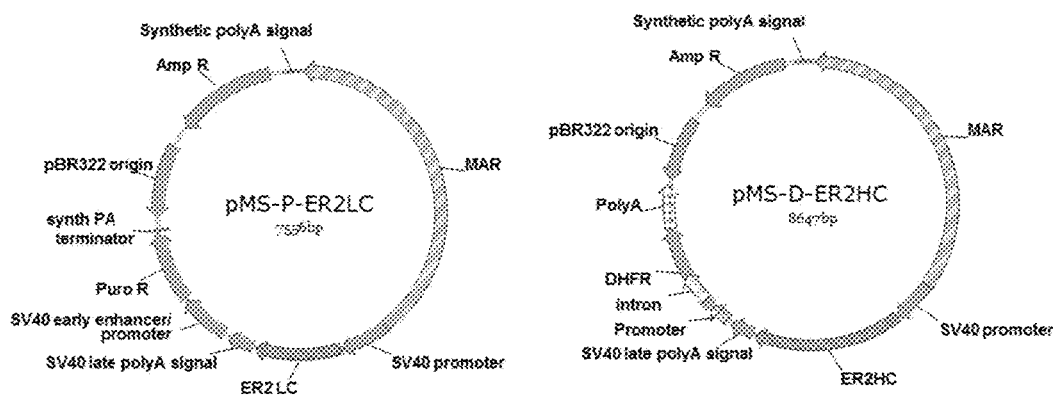
FIGS. 18A and 18B show the structures of a first pair of novel vectors ("novel vector pair I") for ER2 antibody expression (pMS-P-ER2LC and pMS-D-ER2HC), and a pair of MAR vectors (pMSGneo-ER2LC and pMSGneo-ER2HC), respectively.
Figure 18B:
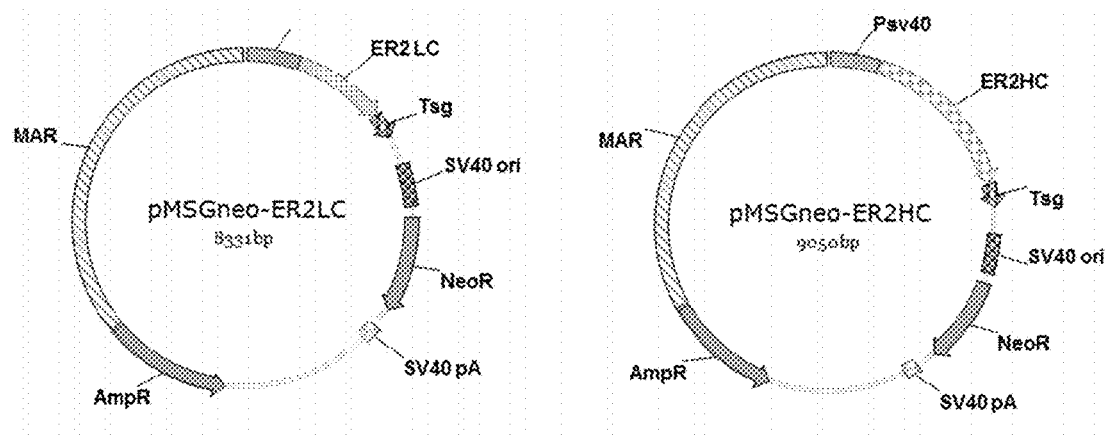

The cloned product was treated with the same restriction enzymes, and it was verified whether the band with a desired size was present on the DNA gel. As such, 4 vectors were prepared, which comprises the novel vector pair I (pMS-P-ER2LC and pMS-D-ER2HC) for ER2 antibody expression and a pair of MAR vectors (pMSGneo-ER2LC and pMS-Gneo-ER2HC) (FIGS. 18A and 18B).

On the other hand, vectors were additionally prepared to verify the effect of adding a chimeric intron to the novel vector pair I prepared above. PCR was carried out using pcDS-dCFH vector as a template and using the primer set of SEQ ID NOs: 44 and 45, to obtain a DNA fragment, and the PCR product was inserted into pCR2.1-TOPO vector, and the DNA sequence of the chimeric intron (SEQ ID NO: 25) was verified. The novel vector pair I for ER2 antibody expression (pMS-P-ER2LC vector and pMS-D-ER2HC vector) was cut with XhoI, and the chimeric introns treated with the same restriction enzymes were respectively inserted thereto. Through the above procedure, the novel vector pair II (pMSI-P-ER2LC and pMSI-D-ER2HC ER2) for ER2 antibody expression was prepared (FIG. 19).

ER2 antibody expression vectors were additionally prepared to verify the element properties of the novel vector pair II.

Figure 20A:
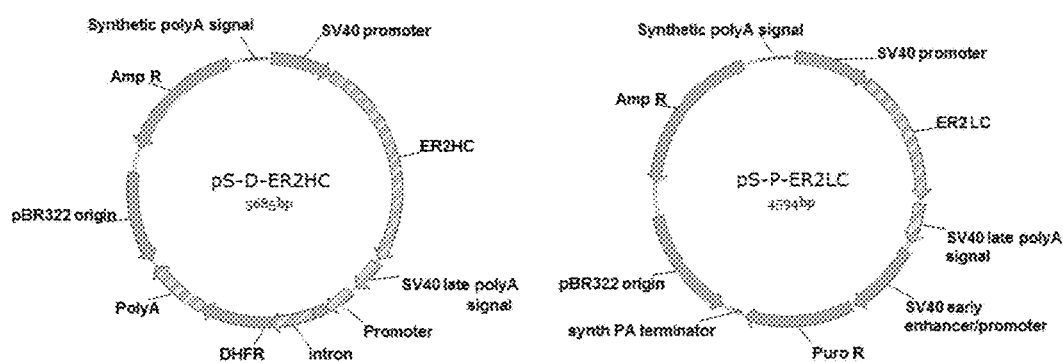
FIGS. 20A and 20B show the structures of a pair of promoter vectors (pS) (pS-P-ER2LC and pS-D-ER2HC), and a pair of intron vectors (pSI-P-ER2LC and pSI-D-ER2HC), respectively.
Figure 20B:
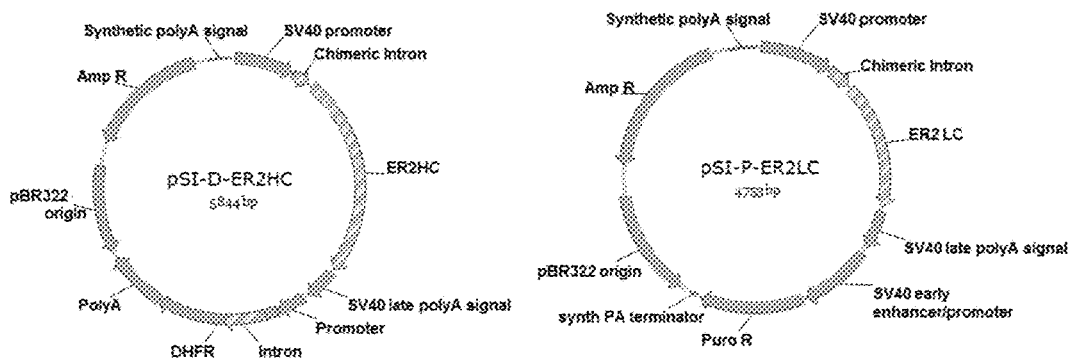

As for the vectors with a SV40 promoter only, pS-P-MCS vector was prepared by removing FIX gene from pGL4.2-SV40-FIX vector by the same method as above, and pS-D-MCS vector was prepared by further replacing the puromycin gene with DHFR gene. Then, the light and heavy chain genes of ER2 were inserted thereto using XhoI and PacI, to prepare a pair of vectors (pS-P-ER2LC and pS-D-ER2HC) for ER2 antibody expression vector with the SV40 promoter (FIG. 20A). Chimeric intron was inserted into the prepared vectors using XhoI restriction enzyme to prepare a pair of vectors (pSI-P-ER2LC and pSI-D-ER2HC) comprising a chimeric intron (FIG. 20B).

Example 3: Evaluation of Gene Expression Ability of Vectors

The gene expression ability of the novel vectors prepared above was verified as follows.

3-1: Evaluation of the Novel Vector Pair I and the Novel Vector Pair II for ER2 Antibody Expression in the Adherent Cell Lines First, ER2 antibody expression using the novel vector pair I and the novel vector pair II were carried out in the CHO-K1 and CHO-DG44 adherent cell lines. The expression levels were compared with a pair of commercial double vectors and a pair of MAR vectors shown in Table 4.

TABLE 4

| Pair of commercial double vectors | pcDNA3.3-ER2HC |
| | pOptiVec-ER2LC |
| Pair of MAR vectors | pMSGneo-ER2LC |
| | pMSGneo-ER2HC |
| | pDCH1p |
| Novel vector pair I | pMS-P-ER2LC |
| | pMS-D-ER2HC |
| Novel vector pair II | pMSI-P-ER2LC |
| | pMSI-D-ER2HC |

24 hrs prior to transfection, CHO-K1 cells being cultured in the DMEM (w/10% FBS) culture medium were dispensed into the wells of a 12-well plate in an amount of 500 μL each at $0.8 \times 10^5$ cells/well. The CHO-DG44 cells being cultured in the MEM-α w/HT (Gibco, 12571-063) culture medium were dispensed into the wells in an amount of 500 μL each at $1.5 \times 10^5$ cells/well. 24 hrs after the dispensing, Opti-MEM and the test vector were mixed in a 1.5 mL tube to the total volume of 50 μL (based on 1 well). 47 μL of Opti-MEM and 3 μL of lipofectamine 2000 were mixed in a new 1.5 mL tube and allowed to react for 5 min at room temperature (based on 1 well). After the reaction was completed, the two kinds of solutions prepared above were mixed and allowed to react for 20 min at room temperature. 24 hrs later, each well was removed of the transfected medium and washed with PBS. Trypsin-EDTA (1×) was dispensed thereto at 100 μL/well and allowed to react for 1 minute at 37° C. to detach the cells. The culture medium was dispensed thereto at 1000 μL/well and the number of cells was counted.

CHO-K1 cells were dispensed into the wells of a 12-well plate at $1.0 \times 10^5$ cells/well to the total volume of 1 mL; 1000 μg/mL of G418 (PAA, P11-012) or 50 μg/mL of puromycin were added thereto appropriately for each vector; and the cell selection was carried out. DG44 cells were dispensed into the wells of a 12-well plate at $1.5 \times 10^5$ cells/well to the total volume of 1 mL; 750 μg/mL of G418 or 20 μg/mL of puromycin were added thereto appropriately for each vector; and the cell selection was carried out. The transfection was conducted in a total of 2 sets, and the samples were obtained in a total of 3 times per set throughout 3 weeks, and the ELISA test was conducted.

ER2 ELSIA method is as follows. Goat anti-human IgG (Fab-specific) (Sigma, 15260) was diluted to 5 μg/mL using a coating buffer. The diluted capture antibodies were dispensed into a 96-well ELISA plate at 100 μL/well, and allowed to react for 2 hrs or longer at room temperature. They were washed 3 times using 300 μL of PBS-0.1% Tween 20 buffer. PBS-1% BSA was added thereto at 300 μL/well, and blocking was carried out for 2 hrs at room temperature. The resultant was washed 3 times using 300 μL of PBS-0.1% Tween 20 buffer. HBIG gene (2.8 mg/mL) as a standard was prepared in the concentrations of 280, 140, 70, 35, 17.5, 8.75 and 4.375 ng/mL using PBS-1% BSA. The culture solutions were diluted using PBS-1% BSA. The standard and diluted culture solutions were dispensed into a 96-well plate coated with the capture antibodies at 100 μL/well in duplication, and allowed to react for 1 hour at room temperature. The wells were washed 3 times using 300 μL of PBS-0.1% Tween 20 buffer. Goat anti-human IgG (Fc specific)-HRP (Sigma, A0170) was diluted to 1/100,000 using PBS-BSA. The diluted solution was dispensed into the plate at 100 μL/well, and allowed to react for 1 hr at room temperature. The resultant was washed 3 times with 300 μL of PBS-0.1% Tween 20 buffer. TMB microwell peroxidase substrate was dispensed at 100 μL/well and allowed to react for 30 min at room temperature. 2.5 M $H_2SO_4$ was dispensed at 100 μL/well to stop the reaction, and the absorbance was measured at 450 nm using a microplate reader. A standard curve was made with 4-parameter fitting, and the measured absorbance of the culture solutions was substituted for parameters, to calculate the concentrations.

Figure 21A:
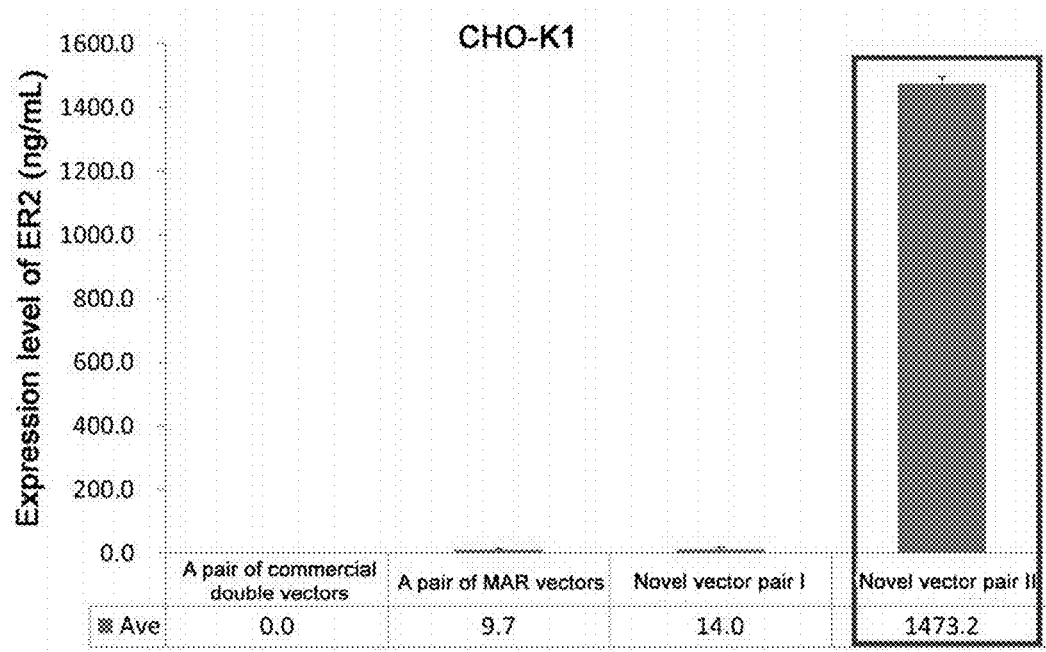
FIGS. 21A and 21B show the ER2 antibody expression levels in the CHO adherent cells CHO-K1 and DG44, respectively.
Figure 21B:
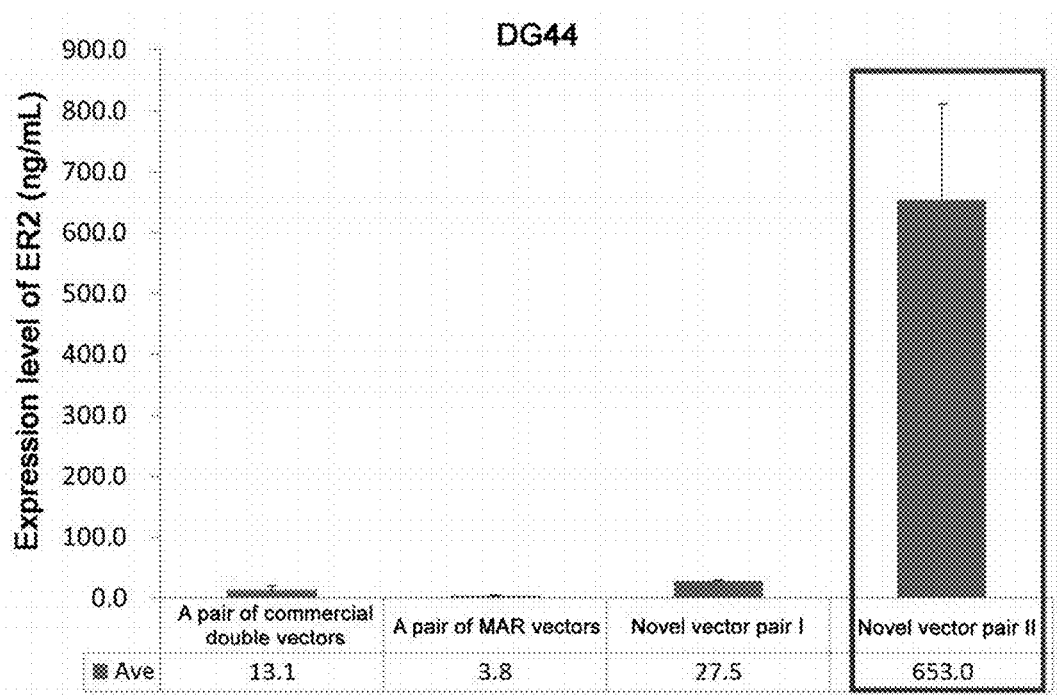

As shown in Table 5, and FIGS. 21A and 21B, the expression level of ER2 Ab in the pair of commercial double vectors in CHO-K1 could not be verified. The pair of conventional MAR vectors, the novel vector pair I, and the novel vector pair II showed the average expression levels of about 9.7 ng/mL, about 14.0 ng/mL, and about 1473.2 ng/mL, respectively. The novel vector pair I and the novel vector pair II showed about 1.4 times and about 151.3 times higher expression levels than a pair of MAR vectors, respectively. In addition, the novel vector pair II showed about 105.4 times higher expression level than the novel vector pair I, which exhibited that the effect of chimeric intron was excellent.

The average expression levels of ER2 Ab of the pair of commercial double vectors, the pair of MAR vectors, the novel vector pair I and the novel vector pair II in CHO DG44 cell were 13.1 ng/mL, 3.8 ng/mL, 27.5 ng/mL and 653.0 ng/mL, respectively. The pair of commercial double vectors showed about 3.5 times higher expression level than the pair of MAR vectors. The novel vector pair I and the novel vector pair II showed about 7.3 and 173.7 times higher expression levels than the pair of MAR vectors, respectively. In addition, the novel vector pair II showed about 23.8 times higher expression level than the novel vector pair I.

TABLE 5

| | ER2 antibody expression level (ng/ml) | | | | | | | |
|---|---|---|---|---|---|---|---|---|
| | CHO-K1 cell | | | | CHO DG44 cell | | | |
| Vector | 1st | 2nd | Ave | SD | 1st | 2nd | Ave | SD |
| Pair of commercial double vectors | 0.0 | 0.0 | 0.0 | 0.0 | 18.2 | 7.9 | 13.1 | 7.3 |
| Pair of conventional MAR vectors | 14.0 | 5.5 | 9.7 | 6.0 | 3.1 | 4.4 | 3.8 | 0.9 |
| Novel vector pair I | 9.4 | 18.6 | 14.0 | 6.5 | 28.8 | 26.1 | 27.5 | 1.9 |
| Novel vector pair II | 1490.7 | 1455.7 | 1473.2 | 24.7 | 764.9 | 541.0 | 653.0 | 158.3 |

3-2: Evaluation of the Novel Vector Pair II in the Suspended Cell Line

The novel vector pair II was evaluated in CHO—S and CD DG44-S suspension cell lines.

The CHO—S cell line (Gibco, A13696-01) was passaged in CD FortiCHO culture medium at $5\sim6\times10^5$ cells/mL to a required amount, 24 hrs prior to the transfection. On the day of transfection, the number and viability (necessarily 95% or higher) of the cells were measured. The cells were dispensed into a 125 mL flask at $1\times10^6$ cells/mL using CD FortiCHO medium (Gibco, A11483-01). 90 μg of the plasmid DNA was mixed with OptiPro™ SFM to the total volume of 1.5 mL 270 μL of PEI MAX (1 μg/μL) and 1230 μL of OptiPro™ SFM were mixed, absolutely without vortexing at all. OptiPro™ SFM containing PEI MAX was put into the OptiPro™ SFM containing plasmid DNA, which were then gently mixed. Then, the resultant was allowed to react for 5 min at room temperature. 3 mL of the produced DNA:PEI complex was added dropwise to the CHO—S cells in the 125 mL flask prepared in advance. The cells were cultured in a $CO_2$ shaking incubator at 37° C. with stirring at 130~150 rpm, and the cell selection was carried out 48 hrs later.

On the other hand, CD DG44-S cell line was prepared by the following method. First, CHO DG44 adherent cell line (cultured in an α-MEM (w/)+10% cFBS medium) was passaged in 50 mL medium using a 125 mL spinner flask with an interval of 2~3 days, using the serum-free medium (HyQ SFM4CHO (Thermo Scientific, Hyclone)+1×HT Supplement), thereby adapting the cells to suspension culture. The adapted cells were subcultured with an interval of 2~3 days, with the replaced medium of EX-CELL™ CD CHO (Sigma, 14361C)/4 mM L-Glutamine/1×HT Supplement medium, thereby adapting the cells to the medium. If the growth of the cells was stable and the viability was maintained at 90% or higher, and the concentration of the cells reached $1\sim2\times10^6$ cells/mL, the CHO DG44-S host cell line was subjected to banking, thereby securing the cell line.

24 hrs prior to the transfection, the cells were passaged in EX-CELL™ CD CHO (Sigma, 14361C) at $5\sim7\times10^5$ cells/mL to a required amount. The cells were dispensed into a 125 mL flask in an amount of 15 mL at $2\times10^6$ cells/mL using a Freestyle CHO medium. 30 μg of plasmid DNA was mixed with 150 mM NaCl to the total volume of 0.75 mL 90 μL of PEI MAX (1 μg/μL) and 150 mM NaCl were mixed, absolutely without vortexing at all. 150 mM NaCl containing PEI MAX was put into 150 mM NaCl containing the plasmid DNA and were gently mixed. The resultant was allowed to react for 5 min at room temperature. 1.5 mL of the produced DNA:PEI complex was added dropwise to CD DG44-S cells in 125 mL flask prepared in advance. The cells were cultured in a $CO_2$ shaking incubator at 37° C. with 130 rpm for 5 hrs, and selection of the cell was carried out 48 hrs later.

In the case of CHO—S, selection of the cell was carried out using the selection medium shown in Table 6.

TABLE 6

| Vector | Composition of CHO-S selection medium |
|---|---|
| Novel vector pair II | CD FortiCHO containing 10 μg/mL puromycin, 50 nM MTX and anti-clumping agent (1:100) |
| MAR, Commercial double vector | CD FortiCHO containing 100 μg/mL G418, 50 nM MTX and anti-clumping agent (1:100) |

First, the number of transfected cells was counted. Using the selection medium suitable for each condition, the cells were dispensed into a T-175 flask in an amount of 50 mL at $5\times10^5$ cells/mL If the number of cells was not enough, the total volume was reduced. The cells were cultured under static conditions in a $CO_2$ incubator at 37° C. 7 days after the selection, the number of cells was counted. If the viability exceeded 30%, the test was proceeded to the next step, but if not, the number of cells was counted after 10~11 days. If the viability was less than 30% even after 11 days, the selection medium was replaced with a new one, and the size of T-flask was reduced such that the concentration became $3\times10^5$ cells/mL or higher. The medium was completely replaced with an interval of 3~4 days, and the recovery signals were checked if any. If the recovery signal was present and the viability was in the range of 30~50%, the cells were passaged in a 125 mL flask at $3\times10^5$ cells/mL using the selection medium suitable for the condition. The cells were cultured in a $CO_2$ incubator at 37° C. with stirring at 150 rpm. With an interval of 3~4 days, the cells were passaged in a 125 flask in an amount of 30 mL at 3×10 cells/mL, using the selection medium suitable for the condition. If the dilution fold was 2-fold or higher, the medium was not refreshed completely. If the viability was 85% or higher and the viable cell density was 1×10⁶ cells/mL or higher, the selection was considered to be completed.

On the other hand, in the case of CD DG44-S, selection of the cell was carried out using the selection medium shown in Table 7.

TABLE 7

| Vector | Composition of CD DG44-S selection medium |
|---|---|
| Novel vector pair II | EX-CELL ™ CD CHO containing 2.5 µg/mL puromycin |
| MAR, Commercial double vector | EX-CELL ™ CD CHO containing 100 µg/mL G418 |

The number of transfected cells was counted. The cells were dispensed into a 125 mL flask in an amount of 30 mL each at 5×10⁵ cells/mL using a selection medium suitable for each vector. If the number of cells was not enough, the total volume was to be reduced. The cells were cultured in a $CO_2$ incubator at 37° C. with stirring at 130 rpm. With an interval of 3~4 days, the cells were passaged in a 125 mL flask in an amount of 30 mL at 3×10⁵ cells/mL using a selection medium. If the dilution fold was 2-fold or higher, the medium was not refreshed completely. If the viability was 80% or higher and the viable cell density was 1×10⁶ cells/mL or higher, the selection was considered to be completed. The transfection was carried out in a total of 2 sets, and the samples were obtained for a total of 3 times throughout 3~4 weeks per each set, and the ELISA test was conducted.

ER2 ELISA was carried out in the same manner as described for the adherent cell lines, and the results are shown in Table 8.

As shown in Table 8 below, regarding the 3 day productivity of ER2 antibody in the CHO—S cell line, the expression levels of the pair of commercial double vectors, the pair of MAR vectors, and the novel vector pair II were 0.2~0.3 µg/mL, 1.0~2.0 µg/mL, and 9.5~17.0 µg/mL (average), respectively. On the batch productivity, the maximum production amounts of the pair of commercial double vectors, the pair of MAR vectors, and the novel vector pair II were 0.7 µg/mL, 10.3 µg/mL, and 35.0 µg/mL (average), respectively. Therefore, on the batch productivity, the novel vector pair II of the present invention showed about 50-fold, and about 3.4-fold or higher antibody expression-increasing effects as compared to the pair of commercial double vectors and the pair of MAR vectors, respectively.

In addition, in the CD DG44-S cell line, regarding the 3 day productivity of ER2 antibody, the expression levels of the pair of commercial double vectors, the pair of MAR vectors, and the novel vector pair II were 0.2~0.3 µg/mL, 0.2~0.25 µg/mL, and 1.0~1.5 µg/mL, respectively. On the batch productivity, the maximum production amounts of the pair of commercial double vectors, the pair of MAR vectors, and the novel vector pair II were 0.7 µg/mL, 0.5 µg/mL, and 3.6 µg/mL (average), respectively.

On the batch productivity, the novel vector pair II showed about 5.1-fold, and about 7.2-fold or higher antibody expression-increasing effects as compared to the pair of commercial double vectors and the pair of MAR vectors, respectively.

TABLE 8

| Cell line | Vector | 3 day productivity (µg/ml) | Period | Batch productivity (µg/ml) |
|---|---|---|---|---|
| CHO-S | Novel vector pair II | 9.5-17.0 | 3.5 wk | <35.0 |
| | Pair of MAR vectors | 1.0-2.0 | 3.5 wk | <10.3 |
| | Pair of commercial double vectors | 0.2-0.3 | 4 wk | <0.7 |
| CD DG44-S | Novel vector pair II | 1.0-1.5 | 3.5 wk | <3.6 |
| | Pair of MAR vectors | 0.2-0.25 | 4 wk | <0.5 |
| | Pair of commercial double vectors | 0.2-0.3 | 4 wk | <0.7 |

3-3: Property Evaluation of Constituting Elements of the Novel Vectors

Property evaluation of the constituting elements of the novel vectors were carried out in CHO—S and CD DG44-S cell lines. As shown in the Table 9 below, the pairs of vectors used in the test were as follows: pS (a pair of promoter vectors), pSI (a pair of intron vectors), pMS (the novel vector pair I) and pMSI (the novel vector pair II).

TABLE 9

| pS (pair of promoter vectors) | pS-P-ER2LC |
| | pS-D-ER2HC |
| pSI (pair of intron vectors) | pSI-P-ER2LC |
| | pSI-D-ER2HC |
| pMS (novel vector pair I) | pMS-P-ER2LC |
| | pMS-D-ER2HC |
| pMSI (novel vector pair II) | pMSI-P-ER2LC |
| | pMSI-D-ER2HC |

The same evaluation method as in Example 3-2 was used as follows. Each pairs of vectors was transfected, and when the selection was completed through the selection period, the ER2 antibody expression levels were compared. The results are shown in Table 10 below.

TABLE 10

| Cell line | Pairs of vectors | 3 day productivity (mg/L) | PCD | Fold (3 days) | Fold (PCD) | Adaptation period (day) |
|---|---|---|---|---|---|---|
| CHO-S (10P50M) | pS | 0.23 | 0.056 | 1.0 | 1.0 | 31 |
| | pSI | 4.21 | 0.747 | 18.4 | 13.3 | 48 |
| | pMS | 0.40 | 0.056 | 1.8 | 1.0 | 27 |
| | pMSI | 4.71 | 1.461 | 20.6 | 26.1 | 27 |
| CD DG44-S (2.5P0M) | pS | 0.02 | 0.002 | 1.0 | 1.0 | 17 |
| | pSI | 0.30 | 0.033 | 13.8 | 14.7 | 17 |
| | pMS | 0.05 | 0.009 | 2.4 | 3.8 | 14 |
| | pMSI | 1.40 | 0.195 | 64.8 | 86.4 | 14 |

As shown in Table 10, in the CHO—S cell line, the cell selections regarding the novel vector pair I, the novel vector pair II, the pair of promoter vectors, and the pair of intron vectors were completed in about 4 weeks, about 4.5 weeks, and about 7 weeks, respectively. The novel vector pair I and the novel vector pair II having a MAR element showed about 1.8 times shorter selection period than the pair of intron vectors. Selection results showed that, as compared to the pair of promotor vectors, the 3 day productivities of the pair of intron vectors, the novel vector pair I and the novel vector pair II were increased 18.4-fold, 1.8-fold, and 20.6-fold, respectively; and PCD (pg/cells/date) of the pair of intron vectors, the novel vector pair I, and the novel vector pair II were increased 13.3-fold, 1.0-fold, and 26.1-fold, respectively.

In the CD DG44-S cell line, selection of the cell regarding the four vectors was all completed in about three weeks. Unlike in CHO—S, all vectors were adapted during similar periods. Also, it was found that, as compared to the pair of promotor vectors, the 3 day productivities of the pair of intron vectors, the novel vector pair I and the novel vector pair II were increased 13.8-fold, 2.4-fold, and 64.8-fold, respectively; and PCD of the pair of intron vectors, the novel vector pair I and the novel vector pair II were increased 14.7-fold, 3.8-fold, and 86.4-fold, respectively.

In conclusion, about 1.6 to 2.0-fold synergistic effects in 3 day productivity and PCD were observed when the MAR element and the intron element were used together rather than separately.

While the present invention has been described with respect to the above specific embodiments, it should be recognized that various modifications and changes may be made to the present invention by those skilled in the art which also fall within the scope of the present invention as defined by the appended claims.

What is claimed is:

1. An expression vector comprising an operably linked simian virus 40 (SV40) promoter, matrix attachment region (MAR) element, and a chimeric intron,
 wherein the MAR element has the sequence of SEQ ID NO: 40 or 41; and
 wherein the expression vector comprises pMSI-P-ER2LC or pMSI-D-ER2HC disclosed in FIG. 19, wherein the ER2LC region of the pMSI-P-ER2LC and the ER2HC region of the pMSI-D-ER2HC are optionally substituted with a target gene.

2. The expression vector according to claim 1, wherein the SV40 promoter has the sequence of SEQ ID NO: 12.

3. The expression vector according to claim 1, wherein the chimeric intron has the sequence of SEQ ID NO: 25.

4. The expression vector according to claim 1, further comprising a locus control region (LCR) element having the sequence of SEQ ID NO: 15 or 16.

5. The expression vector of claim 1, wherein the target gene is selected from the group consisting of:
 factor VII (FVII) gene, factor VIII (FVIII) gene, factor IX (FIX) gene, epidermal growth factor receptor family antibody gene, insulin gene, interleukin gene, tumor necrosis factor gene, interferon gene, colony stimulating factor gene, chemokine gene, erythropoietin gene, α-fetoprotein gene, a-glucosidase gene, al-antitrypsin gene, antithrombin gene, lipoprotein gene, celluloplasmin gene, fibrinogen gene, glucocerebrosidase gene, haptoglobin gene, plasminogen gene, prothrombin gene, and transferrin gene.

6. A cell transformed by the expression vector of claim 1.

7. The cell of claim 6, wherein the cell is selected from the group consisting of CHO-K1 cell, CHO-DG44 cell, CHO-S cell, CHO DUKX-B11 cell, COST cell, COS3 cell, COS1 cell, NSO cell, HeLa cell, Vero cell, PER-C6 cell, HepG2 cell, and BHK cell.

8. A method for producing a target protein comprising:
culturing cells transformed by the expression vector of claim 1 to express the target protein; and
recovering the target protein.

9. A cell transformed by the expression vector of claim 2.

10. A cell transformed by the expression vector of claim 3.

11. A cell transformed by the expression vector of claim 4.

12. A cell transformed by the expression vector of claim 5.

13. A method for producing a target protein comprising:
culturing cells transformed by the expression vector of claim 5 to express the target protein; and
recovering the target protein.

* * * * *

SEQUENCE LISTING

```
<160> NUMBER OF SEQ ID NOS: 52

<210> SEQ ID NO 1
<211> LENGTH: 31
<212> TYPE: DNA
<213> ORGANISM: Artificial Sequence
<220> FEATURE:
<223> OTHER INFORMATION: PCR Forward primer for DNA fragment comprising
      CMV promoter

<400> SEQUENCE: 1
agctagcgtt gacattgatt attgactagt t                                      31

<210> SEQ ID NO 2
<211> LENGTH: 31
<212> TYPE: DNA
<213> ORGANISM: Artificial Sequence
<220> FEATURE:
<223> OTHER INFORMATION: PCR reverse primer for DNA fragment comprising
      CMV promoter

<400> SEQUENCE: 2
gctcgagagc tctgcttata tagacctccc a                                      31

<210> SEQ ID NO 3
<211> LENGTH: 27
<212> TYPE: DNA
<213> ORGANISM: Artificial Sequence
<220> FEATURE:
<223> OTHER INFORMATION: PCR Forward primer for Scaffold attachment
      region (SAR)

<400> SEQUENCE: 3
aggtaccgga tcccattctc cttgatg                                           27

<210> SEQ ID NO 4
<211> LENGTH: 27
<212> TYPE: DNA
<213> ORGANISM: Artificial Sequence
<220> FEATURE:
<223> OTHER INFORMATION: PCR reverse primer for SAR

<400> SEQUENCE: 4
agctagcgga tccgaattca aacaact                                           27

<210> SEQ ID NO 5
<211> LENGTH: 33
<212> TYPE: DNA
<213> ORGANISM: Artificial Sequence
<220> FEATURE:
<223> OTHER INFORMATION: PCR Forward primer for MAR2.2

<400> SEQUENCE: 5
aggatccgct agcaagttgt taaggagccc ttt                                    33
```

```
<210> SEQ ID NO 6
<211> LENGTH: 35
<212> TYPE: DNA
<213> ORGANISM: Artificial Sequence
<220> FEATURE:
<223> OTHER INFORMATION: PCR reverse primer for MAR2.2

<400> SEQUENCE: 6
aggatccggt acccctcctg agtagctggg gacta                              35

<210> SEQ ID NO 7
<211> LENGTH: 33
<212> TYPE: DNA
<213> ORGANISM: Artificial Sequence
<220> FEATURE:
<223> OTHER INFORMATION: PCR Forward primer for MAR3.0

<400> SEQUENCE: 7
ggatccgcta gcttttcctc tttaggttct cct                                33

<210> SEQ ID NO 8
<211> LENGTH: 34
<212> TYPE: DNA
<213> ORGANISM: Artificial Sequence
<220> FEATURE:
<223> OTHER INFORMATION: PCR reverse primer for MAR3.0

<400> SEQUENCE: 8
aggatccggt acccctcctg agtagctggg gact                               34

<210> SEQ ID NO 9
<211> LENGTH: 27
<212> TYPE: DNA
<213> ORGANISM: Artificial Sequence
<220> FEATURE:
<223> OTHER INFORMATION: PCR Forward primer for DNA fragment comprising
     SV40 promoter

<400> SEQUENCE: 9
agctagcgcg cagcaccatg gcctgaa                                       27

<210> SEQ ID NO 10
<211> LENGTH: 27
<212> TYPE: DNA
<213> ORGANISM: Artificial Sequence
<220> FEATURE:
<223> OTHER INFORMATION: PCR reverse primer for DNA fragment comprising
     SV40 promoter

<400> SEQUENCE: 10
actcgaggag cttttttgcaa aagccta                                      27

<210> SEQ ID NO 11
<211> LENGTH: 588
<212> TYPE: DNA
<213> ORGANISM: Artificial Sequence
<220> FEATURE:
<223> OTHER INFORMATION: CMV promoter

<400> SEQUENCE: 11
gttgacattg attattgact agttattaat agtaatcaat tacggggtca ttagttcata    60
gcccatatat ggagttccgc gttacataac ttacggtaaa tggcccgcct ggctgaccgc   120
ccaacgaccc ccgcccattg acgtcaataa tgacgtatgt tcccatagta acgccaatag   180
ggactttcca ttgacgtcaa tgggtggagt atttacggta aactgcccac ttggcagtac   240
```

| | |
|---|---|
| atcaagtgta tcatatgcca agtacgcccc ctattgacgt caatgacggt aaatggcccg | 300 |
| cctggcatta tgcccagtac atgaccttat gggactttcc tacttggcag tacatctacg | 360 |
| tattagtcat cgctattacc atggtgatgc ggttttggca gtacatcaat gggcgtggat | 420 |
| agcggtttga ctcacgggga tttccaagtc tccaccccat tgacgtcaat gggagtttgt | 480 |
| tttggcacca aaatcaacgg gactttccaa aatgtcgtaa caactccgcc ccattgacgc | 540 |
| aaatgggcgg taggcgtgta cggtgggagg tctatataag cagagctc | 588 |

```
<210> SEQ ID NO 12
<211> LENGTH: 419
<212> TYPE: DNA
<213> ORGANISM: Artificial Sequence
<220> FEATURE:
<223> OTHER INFORMATION: SV40 promoter

<400> SEQUENCE: 12
```

| | |
|---|---|
| gcgcagcacc atggcctgaa ataacctctg aaagaggaac ttggttagct accttctgag | 60 |
| gcggaaagaa ccagctgtgg aatgtgtgtc agttaggggtg tggaaagtcc ccaggctccc | 120 |
| cagcaggcag aagtatgcaa agcatgcatc tcaattagtc agcaaccagg tgtggaaagt | 180 |
| ccccaggctc cccagcaggc agaagtatgc aaagcatgca tctcaattag tcagcaacca | 240 |
| tagtcccgcc cctaactccg cccatcccgc cctaactccg cccagttccg cccattctc | 300 |
| cgccccatgg ctgactaatt ttttttattt atgcagaggc cgaggccgcc tctgcctctg | 360 |
| agctattcca gaagtagtga ggaggctttt ttggaggcct aggcttttgc aaaaagctc | 419 |

```
<210> SEQ ID NO 13
<211> LENGTH: 120
<212> TYPE: DNA
<213> ORGANISM: Artificial Sequence
<220> FEATURE:
<223> OTHER INFORMATION: alpha-1-antitrypsin precursor, AAT 108

<400> SEQUENCE: 13
```

| | |
|---|---|
| cgactcagat cccagccagt ggacttagcc cctgtttgct cctccgataa ctggggtgac | 60 |
| cttggttaat attcaccagc agcctccccc gttgcccctc tggatccact gcttaaatac | 120 |

```
<210> SEQ ID NO 14
<211> LENGTH: 81
<212> TYPE: DNA
<213> ORGANISM: Artificial Sequence
<220> FEATURE:
<223> OTHER INFORMATION: Serum albumin preproprotein, Alb E6

<400> SEQUENCE: 14
```

| | |
|---|---|
| agctttctga acagccaaac agagattcca aagttcaggc accaaagttc agaccctaac | 60 |
| agttatttac aagggtcagt t | 81 |

```
<210> SEQ ID NO 15
<211> LENGTH: 480
<212> TYPE: DNA
<213> ORGANISM: Artificial Sequence
<220> FEATURE:
<223> OTHER INFORMATION: AAT 108x4

<400> SEQUENCE: 15
```

| | |
|---|---|
| cgactcagat cccagccagt ggacttagcc cctgtttgct cctccgataa ctggggtgac | 60 |
| cttggttaat attcaccagc agcctccccc gttgcccctc tggatccact gcttaaatac | 120 |
| cgactcagat cccagccagt ggacttagcc cctgtttgct cctccgataa ctggggtgac | 180 |

```
cttggttaat attcaccagc agcctccccc gttgcccctc tggatccact gcttaaatac    240
cgactcagat cccagccagt ggacttagcc cctgtttgct cctccgataa ctggggtgac    300
cttggttaat attcaccagc agcctccccc gttgcccctc tggatccact gcttaaatac    360
cgactcagat cccagccagt ggacttagcc cctgtttgct cctccgataa ctggggtgac    420
cttggttaat attcaccagc agcctccccc gttgcccctc tggatccact gcttaaatac    480
```

<210> SEQ ID NO 16
<211> LENGTH: 324
<212> TYPE: DNA
<213> ORGANISM: Artificial Sequence
<220> FEATURE:
<223> OTHER INFORMATION: Alb E6x4

<400> SEQUENCE: 16

```
agctttctga acagccaaac agagattcca agttcaggc accaaagttc agaccctaac     60
agttatttac aagggtcagt tagctttctg aacagccaaa cagagattcc aaagttcagg   120
caccaaagtt cagaccctaa cagttattta caagggtcag ttagctttct gaacagccaa   180
acagagattc caaagttcag gcaccaaagt tcagaccta acagttattt acaagggtca    240
gttagctttc tgaacagcca aacagagatt ccaaagttca ggcaccaaag ttcagaccct   300
aacagttatt tacaagggtc agtt                                          324
```

<210> SEQ ID NO 17
<211> LENGTH: 29
<212> TYPE: DNA
<213> ORGANISM: Artificial Sequence
<220> FEATURE:
<223> OTHER INFORMATION: PCR Forward primer for Alb E6x1

<400> SEQUENCE: 17

```
atggtaccgg atccagcttt ctgaacagc                                      29
```

<210> SEQ ID NO 18
<211> LENGTH: 29
<212> TYPE: DNA
<213> ORGANISM: Artificial Sequence
<220> FEATURE:
<223> OTHER INFORMATION: PCR reverse primer for Alb E6x1

<400> SEQUENCE: 18

```
aggctagcgg atccaactga cccttgtaa                                      29
```

<210> SEQ ID NO 19
<211> LENGTH: 31
<212> TYPE: DNA
<213> ORGANISM: Artificial Sequence
<220> FEATURE:
<223> OTHER INFORMATION: PCR Forward primer for AAT 108x1

<400> SEQUENCE: 19

```
atatggtacc agatctcgac tcagatccca g                                   31
```

<210> SEQ ID NO 20
<211> LENGTH: 31
<212> TYPE: DNA
<213> ORGANISM: Artificial Sequence
<220> FEATURE:
<223> OTHER INFORMATION: PCR reverse primer for AAT 108x1

<400> SEQUENCE: 20

```
ggctgctagc agatctgtat ttaagcagtg g                                    31

<210> SEQ ID NO 21
<211> LENGTH: 35
<212> TYPE: DNA
<213> ORGANISM: Artificial Sequence
<220> FEATURE:
<223> OTHER INFORMATION: SCR 1 F primer

<400> SEQUENCE: 21
tagcggccgc catgagactt ctagcaaaga ttatt                                35

<210> SEQ ID NO 22
<211> LENGTH: 30
<212> TYPE: DNA
<213> ORGANISM: Artificial Sequence
<220> FEATURE:
<223> OTHER INFORMATION: SCR5(18) B primer

<400> SEQUENCE: 22
acaggaggtg tcacatctcg gagcaggtat                                      30

<210> SEQ ID NO 23
<211> LENGTH: 31
<212> TYPE: DNA
<213> ORGANISM: Artificial Sequence
<220> FEATURE:
<223> OTHER INFORMATION: SCR18(5) F primer

<400> SEQUENCE: 23
gctccgagat gtgacacctc ctgtgtgaat c                                    31

<210> SEQ ID NO 24
<211> LENGTH: 30
<212> TYPE: DNA
<213> ORGANISM: Artificial Sequence
<220> FEATURE:
<223> OTHER INFORMATION: SCR 20 B primer

<400> SEQUENCE: 24
cgcctcgagc tatcttttg cacaagttgg                                       30

<210> SEQ ID NO 25
<211> LENGTH: 133
<212> TYPE: DNA
<213> ORGANISM: Artificial Sequence
<220> FEATURE:
<223> OTHER INFORMATION: chimeric intron, gene bank #JQ795930

<400> SEQUENCE: 25
gtaagtatca aggttacaag acaggtttaa ggagaccaat agaaactggg cttgtcgaga     60
cagagaagac tcttgcgttt ctgataggca cctattggtc ttactgacat ccactttgcc   120
tttctctcca cag                                                      133

<210> SEQ ID NO 26
<211> LENGTH: 542
<212> TYPE: DNA
<213> ORGANISM: Artificial Sequence
<220> FEATURE:
<223> OTHER INFORMATION: WPRE gene

<400> SEQUENCE: 26
aatcaacctc tggattacaa aatttgtgaa agattgactg gtattcttaa ctatgttgct     60
ccttttacgc tatgtggata cgctgcttta atgcctttgt atcatgctat tgcttcccgt   120
```

```
atggctttca ttttctcctc cttgtataaa tcctggttgc tgtctcttta tgaggagttg    180
tggcccgttg tcaggcaacg tggcgtggtg tgcactgtgt ttgctgacgc aaccccact    240 ggttggggca ttgccaccac ctgtcagctc ctttccggga ctttcgcttt cccctccct    300 attgccacgg cggaactcat cgccgcctgc cttgcccgct gctggacagg ggctcggctg    360
ttgggcactg acaattccgt ggtgttgtcg gggaagctga cgtcctttcc atggctgctc    420
gcctgtgttg ccacctggat tctgcgcggg acgtccttct gctacgtccc ttcggccctc    480
aatccagcgg accttccttc ccgcggcctg ctgccggctc tgcggcctct tccgcgtctt    540
cg                                                                   542
```

```
<210> SEQ ID NO 27
<211> LENGTH: 23
<212> TYPE: DNA
<213> ORGANISM: Artificial Sequence
<220> FEATURE:
<223> OTHER INFORMATION: WPRE F primer

<400> SEQUENCE: 27
cactcgagaa tcaacctctg gat                                            23

<210> SEQ ID NO 28
<211> LENGTH: 23
<212> TYPE: DNA
<213> ORGANISM: Artificial Sequence
<220> FEATURE:
<223> OTHER INFORMATION: WPRE B primer

<400> SEQUENCE: 28
attctagacg aagacgcgga aga                                            23

<210> SEQ ID NO 29
<211> LENGTH: 39
<212> TYPE: DNA
<213> ORGANISM: Artificial Sequence
<220> FEATURE:
<223> OTHER INFORMATION: PCR Forward primer for FIX expression vector

<400> SEQUENCE: 29
actcgagtta attaagggcc catgcagcgc gtgaacatg                           39

<210> SEQ ID NO 30
<211> LENGTH: 33
<212> TYPE: DNA
<213> ORGANISM: Artificial Sequence
<220> FEATURE:
<223> OTHER INFORMATION: PCR Reverse primer for FIX expression vector

<400> SEQUENCE: 30
cggccggccg ggccctcatt aagtgagctt tgt                                 33

<210> SEQ ID NO 31
<211> LENGTH: 1705
<212> TYPE: DNA
<213> ORGANISM: Artificial Sequence
<220> FEATURE:
<223> OTHER INFORMATION: FIX gene

<400> SEQUENCE: 31
atgcagcgcg tgaacatgat catggcagaa tcaccaggcc tcatcaccat ctgcctttta    60
ggatatctac tcagtgctga atgtacaggt ttgtttgtcg acccttttt aaaatacatt    120
```

-continued

```
gagtatgctt gccttttaga tatagaaata tctgatgctg tcttcttcac taaattttga      180
ttacatgatt tgacagcaat attgaagagt ctaacagcca gcacgcaggt tggtaacgcg      240
tgtactgtgg aacatcaca gattttggct ccatgccta aagagaaatt ggctttcaga       300
ttatttggat taaaaacaaa gactttctta agagatgtaa aattttcatg atgttttctt     360
ttttgctaaa actaaagaat taactagttt cttttacatt tcagtttttc ttgatcatga     420
aaacgccaac aaaattctga atcggccaaa gaggtataat tcaggtaaat tggaagagtt     480
tgttcaaggg aaccttgaga gagaatgtat ggaagaaaag tgtagttttg aagaagcacg     540
agaagttttt gaaaacactg aaagaacaac tgaattttgg aagcagtatg ttgatggaga    600
tcagtgtgag tccaatccat gtttaaatgg cggcagttgc aaggatgaca ttaattccta    660
tgaatgttgg tgtcccttg gatttgaagg aaagaactgt gaattagatg taacatgtaa     720
cattaagaat ggcagatgcg agcagttttg taaaaatagt gctgataaca aggtggtttg    780
ctcctgtact gagggatatc gacttgcaga aaaccagaag tcctgtgaac cagcagtgcc    840
atttccatgt ggaagagttt ctgtttcaca aacttctaag ctcacccgtg ctgaggctgt    900
ttttcctgat gtggactatg taaattctac tgaagctgaa accattttgg ataacatcac    960
tcaaagcacc caatcattta tgacttcac tcgggttgtt ggtggagaag atgccaaacc    1020
aggtcaattc ccttggcagg ttgttttgaa tggtaaagtt gatgcattct gtggaggctc    1080
tatcgttaat gaaaaatgga ttgtaactgc tgcccactgt gttgaaactg tgttaaaat    1140 tacagttgtc gcaggtgaac ataatattga ggagacagaa catacagagc aaaagcgaaa   1200
tgtgattcga attattcctc accacaacta caatgcagct attaataagt acaaccatga   1260
cattgccctt ctggaactgg acgaaccctt agtgctaaac agctacgtta cacctatttg   1320
cattgctgac aaggaataca cgaacatctt cctcaaattt ggatctggct atgtaagtgg   1380
ctggggaaga gtcttccaca aagggagatc agctttagtt cttcagtacc ttagagttcc   1440
acttgttgac cgagccacat gtcttcgatc tacaaagttc accatctata caacatgtt    1500 ctgtgctggc ttccatgaag gaggtagaga ttcatgtcaa ggagatagtg ggggacccca   1560
tgttactgaa gtgaagggaa ccagtttctt aactggaatt attagctggg gtgaagagtg   1620
cgcaatgaaa ggcaaatatg gaatatatac caaggtatcc cggtatgtca actggattaa   1680
ggaaaaaaca aagctcactt aatga                                          1705
```

<210> SEQ ID NO 32
<211> LENGTH: 32
<212> TYPE: DNA
<213> ORGANISM: Artificial Sequence
<220> FEATURE:
<223> OTHER INFORMATION: PCR forward primer for DHFR expression system

<400> SEQUENCE: 32
agctcttccg ctgcgcacgc cgcgactggg cg       32

<210> SEQ ID NO 33
<211> LENGTH: 30
<212> TYPE: DNA
<213> ORGANISM: Artificial Sequence
<220> FEATURE:
<223> OTHER INFORMATION: PCR reverse primer for DHFR expression system

<400> SEQUENCE: 33
tgtcgaccat gctctcaggg gctctatgtc       30

<210> SEQ ID NO 34
<211> LENGTH: 1508
<212> TYPE: DNA
<213> ORGANISM: Artificial Sequence
<220> FEATURE:
<223> OTHER INFORMATION: DHFR gene

<400> SEQUENCE: 34

```
gcgcacgccg cgactgggcg gggccggcct ggtggaggcg gagtctgacc tcgtggaggc      60
ggggcctctg atgttcaaat aggatgctag gcttgttgag ggcgtggcct ccgattcaca     120
agtgggaagc agcgccgggc gactgcaatt tcgcgccaaa cttgggggaa gcacagcgta     180
caggctgcct aggtgatcgc tgctgctgtc atggttcgac cgctgaactg catcgtcgcc     240
gtgtcccaga atatgggcat cggcaagaac ggagaccttc cctggccaat gctcaggtac     300
tggctggatt gggttaggga accgaggcg ttcgctgaa tcgggtcgag cacttggcgg      360
agacgcgcgg gccaactact tagggacagt catgaggggt aggcccgccg gctgcagccc     420
ttgcccatgc ccgcggtgat ccccatgctg tgccagcctt gcccagagg cgctctagct      480
gggagcaaag tccggtcact gggcagcacc acccccgga cttgcatggg tagccgctga      540
gatggagcct gagcacacgt gacagggtcc ctgttaacgc agtgtttctc taactttcag     600
gaacgaattc aagtacttcc aaagaatgac caccacctcc tcagtggaag gtaaacagaa     660
cctggtgatt atgggccgga aaacctggtt ctccattcct gagaagaatc gacctttaaa     720
ggacagaatt aatatagttc tcagtagaga gctcaaggaa ccaccacaag gagctcattt     780
tcttgccaaa agtctggacg atgccttaaa acttattgaa caaccagagt tagcagataa     840
agtggacatg gtttggatag ttggaggcag ttccgtttac aaggaagcca tgaatcagcc     900
aggccatctc agactctttg tgacaaggat catgcaggaa tttgaaagtg acacgttctt     960
cccagaaatt gatttggaga aatataaact tctcccagag tacccagggg tccttcctga    1020
agtccaggag gaaaaaggca tcaagtataa atttgaagtc tatgagaaga aggctaaca    1080
gaaagatact tgctgattga cttcaagttc tactgctttc ctcctaaaat tatgcatttt    1140
tacaagacca tgggacttgt gttggcttta gatctatgag ttattctttc tttagagagg    1200
gatagttagg aagatgtatt tgttttgtgg taccagagat ggaacctggg atcctgtgca    1260
tcctgggcaa ctgttgtact ctaagccact ccccaaagtc atgccccagc cctgtataa    1320
ttctaaacaa ttagaattat tttcatttc attagtctaa ccaggttata ttaaatatac    1380
tttaagaaac accatttgcc ataaagttct caatgcccct cccatgcagc ctcaagtggc    1440
tccccagcag atgcataggg tagtgtgtgt acaagagacc caaagacat agagcccctg    1500
agagcatg                                                              1508
```

<210> SEQ ID NO 35
<211> LENGTH: 34
<212> TYPE: DNA
<213> ORGANISM: Artificial Sequence
<220> FEATURE:
<223> OTHER INFORMATION: PCR forward primer for EGFR(ER2) antibody heavy
      chain

<400> SEQUENCE: 35

```
atctcgaggc tagccggccg ccagtgtgct ggaa                                   34
```

<210> SEQ ID NO 36
<211> LENGTH: 36
<212> TYPE: DNA
<213> ORGANISM: Artificial Sequence
<220> FEATURE:
<223> OTHER INFORMATION: PCR reverse primer for EGFR(ER2) antibody heavy chain

<400> SEQUENCE: 36

```
atctcgagtt aattaactat ttacccggag acaggg                                   36
```

<210> SEQ ID NO 37
<211> LENGTH: 34
<212> TYPE: DNA
<213> ORGANISM: Artificial Sequence
<220> FEATURE:
<223> OTHER INFORMATION: PCR forward primer for EGFR(ER2) antibody light chain

<400> SEQUENCE: 37

```
atctcgaggc tagccggagc aagatggatt caca                                     34
```

<210> SEQ ID NO 38
<211> LENGTH: 36
<212> TYPE: DNA
<213> ORGANISM: Artificial Sequence
<220> FEATURE:
<223> OTHER INFORMATION: PCR reverse primer for EGFR(ER2) antibody light chain

<400> SEQUENCE: 38

```
atctcgagtt aattaactaa cactccccccc tgttga                                  36
```

<210> SEQ ID NO 39
<211> LENGTH: 1233
<212> TYPE: DNA
<213> ORGANISM: Artificial Sequence
<220> FEATURE:
<223> OTHER INFORMATION: Human CSP-B Scaffold attachment region (SAR)

<400> SEQUENCE: 39

```
ggatcccatt ctccttgatg tactaatttt tctttaaaag tgataataat agctcccatt         60
tagaattttt aaataacaca acaaatgtaa agtaactaat gtgtcctctg gatcatggta        120
agtaatgaat aaatttaact ccctttacct tctcccttg  ctattttttc catgctagga        180
tttatacatt tttaaaaaac taaatctgct atcaaatgac agctttaaat ttacttttta        240
aaatttgtta ttgtatatat ttatggggta taaagtgatg ttatgatata tatatacaca        300
atgtacactg attaaatcaa gccaattaac attttatcat ctcaaatact taacattttt        360
tgtagtgaga acatttgaaa tttacttttta gcaatttcaa aacatacatt attattatta       420
actatagtca ccatgatgta ccatagatct ttaaaaactt attcttcctg cctaactgaa        480
actttgtact ctttgactaa catctttca  ttccccccact tcccagcctc tggtaatcac       540
cattacacac tctgcttcta tgagttcaat tgctttagac tccacgtaat aaatgagatc        600
atgcagcatt tggctttctg tgcctggctt atccttgctt agcatggtgt cttacaggtt        660
catccatgtt gcaacaaata acagaatctc attctttgtt aaggctgaat actattccat        720
tgggtatata taccacattt tccttatcca ttaatccact gatggaccct taggttgttg        780
attccatata ttggctattg taaatagtgc agcaatgaac atgagagtgc aactatctct        840
tcaatgtact gatttcgaat ccttcggatc tatctcagaa gtgagattgc aggatcatat        900
aattctactt ttagtctttt gaggagctcc atacagcttt ccatatggcc atactaatta        960
cattctcatc aacagtgtac aatggttccc ttttctccac atcctcacca acatttataa       1020
ttttttgtct ttttgataat agccatctga caggtgtaaa gtgatagctc attgcagttt      1080
```

```
taatttgcat tttttgatga ttagtaatgt tgagaattt ttcatatatc tcttggccag   1140
ttgcatgtct tctttggaaa aatgtctatt cagttccttt gcccatttt taattgggat   1200 ttttggtttc ttgctattga gttgtttgaa ttc                               1233
```

<210> SEQ ID NO 40
<211> LENGTH: 2248
<212> TYPE: DNA
<213> ORGANISM: Artificial Sequence
<220> FEATURE:
<223> OTHER INFORMATION: Human betaglobin MAR fragment, MAR2.2

<400> SEQUENCE: 40

```
aagttgttaa ggagcccttt tgattgaagg tgggtgcccc caccttacag ggacaggaca     60
tctggatact cctcccagtt tctccagttt ccctttttcc taatatatct cctgataaaa    120
tgtctatact cacttcccca tttctaataa taaagcaaag gctagttagt aagacatcac    180
cttgcatttt gaaaatgcca tagactttca aaatcatttc atacatcggt ctttctttat    240
ttcaagagtc cagaaatggc aacattacct ttgattcaat gtaatggaaa gagctctttc    300
aagagacaga gaaaagaata atttaatttc tttccccaca cctccttccc tgtctcttac    360
cctatcttcc ttccttctac cctcccccatt tctctctctc atttctcaga agtatatttt   420
gaaaggattc atagcagaca gctaaggctg gttttttcta agtgaagaag tgatattgag    480
aaggtagggt tgcatgagcc ctttcagttt tttagtttat atacatctgt attgttagaa    540
tgttttataa tataaataaa attatttctc agttatatac tagctatgta acttgtggat    600
atttccttaa gtattacaag ctatacttaa ctcacttgga aaactcaaat aaatacctgc    660
ttcatagtta ttaataagga ttaagtgaga taatgcccat aagattccta ttaataacag    720
ataaatacat acacacacac acacattgaa aggattctta ctttgtgcta ggaactataa    780
taagttcatt gatgcattat atcattaagt tctaatttca acactagaag gcaggtatta    840 tctaaattc atactggata cctccaaact cataaagata attaaattgc cttttgtcat    900
atatttattc aaaagggtaa actcaaacta tggcttgtct aatttatat atcaccctac    960 tgaacatgac cctattgtga tatttataa aattattctc aagttattat gaggatgttg   1020
aaagacagag aggatggggt gctatgcccc aaatcagcct cacaattaag ctaagcagct   1080
aagagtcttg cagggtagtg tagggaccac agggttaagg gggcagtaga attatactcc   1140
cactttagtt tcatttcaaa caatccatac acacacagcc ctgagcactt acaaattata   1200
ctacgctcta tactttttgt ttaaatgtat aaataagtgg atgaaagaat agatagatag   1260
acagatagat gatagataga ataaatgctt gccttcatag ctgtctccct accttgttca   1320
aaatgttcct gtccagacca aagtaccttg ccttcactta gtaatcaat tcctaggtta   1380 tattctgatg tcaaaggaag tcaaagatg tgaaaaacaa tttctgaccc caactcatg    1440 ctttgtagat gactagatca aaaaatttca gccatatctt aacagtgagt gaacaggaaa   1500
tctcctcttt tccctacatc tgagatccca gcttctaaga ccttcaatac tcactcttga   1560
tgcaacagac cttggaagta tacaggagag ctgaacttgg tcaacaaagg agaaaagttt   1620
gttggcctcc aaaggcacag ctcaaacttt tcaagccttc tctaatctta aggtaaaca    1680 agggtctcat ttctttgaga acttcaggga aaatagacaa ggacttgcct ggtgcttttg   1740
gtaggggagc ttgcactttc ccccttctg gaggaaatat ttatccccag gtagttccct   1800
ttttgcacca gtggttcttt gaagagactt ccacctggga acagttaaac agcaactaca   1860
```

| | |
|---|---|
| gggccttgaa ctgcacactt tcagtccggt cctcacagtt gaaaagacct aagcttgtgc | 1920 |
| ctgatttaag ccttttttggt cataaaacat tgaattctaa tctccctctc aaccctacag | 1980 |
| tcacccattt ggtatattaa agatgtgttg tctactgtct agtatccctc aagtagtgtc | 2040 |
| aggaattagt catttaaata gtctgcaagc caggagtggt ggctcatgtc tgtaattcca | 2100 |
| gcactggaga ggtagaagtg ggaggactgc ttgagctcaa gagtttgata ttatcctgga | 2160 |
| caacatagca agacctcgtc tctacttaaa aaaaaaaaaa ttagccaggc atgtgatgta | 2220 |
| cacctgtagt ccccagctac tcaggagg | 2248 |

<210> SEQ ID NO 41
<211> LENGTH: 2969
<212> TYPE: DNA
<213> ORGANISM: Artificial Sequence
<220> FEATURE:
<223> OTHER INFORMATION: Human betaglobin MAR fragment, MAR3.0

<400> SEQUENCE: 41

| | |
|---|---|
| ttttcctctt taggttctcc tttatggaat cttctgtact gatggccatg tcctttaact | 60 |
| actatgtaga tatctgctac tacctgtatt atgcctctac ctttattagc agagttatct | 120 |
| gtactgttgg catgacaatc atttgttaat atgacttgcc tttccttttt ctgctattct | 180 |
| tgatcaaatg gctcctcttt cttgctcctc tcatttctcc tgccttcact tggacgtgct | 240 |
| tcacgtagtc tgtgcttatg actggattaa aaattgatat ggacttatcc taatgttgtt | 300 |
| cgtcataata tgggttttat ggtccattat tatttcctat gcattgatct ggagaaggct | 360 |
| tcaatccttt tactctttgt ggaaaatatc tgtaaacctt ctggttcact ctgctatagc | 420 |
| aatttcagtt taggctagta agcatgagga tgcctccttc tctgattttt cccacagtct | 480 |
| gttggtcaca gaataacctg agtgattact gatgaaagag tgggaatgtt attgatagtc | 540 |
| acaatgacaa aaaacaaaca actacagtca aaatgtttct cttttttatta gtggattata | 600 |
| tttcctgacc tatatctggc aggactcttt agagaggtag ctgaagctgc tgttatgacc | 660 |
| actagaggga agaagatacc tgtggagcta atggtccaag atggtggagc cccaagcaag | 720 |
| gaagttgtta aggagccctt ttgattgaag gtgggtgccc ccaccttaca gggacaggac | 780 |
| atctggatac tcctcccagt ttctccagtt tccctttttc ctaatatatc tcctgataaa | 840 |
| atgtctatac tcacttcccc atttctaata ataaagcaaa ggctagttag taagacatca | 900 |
| ccttgcattt tgaaaatgcc atagactttc aaaatcattt catacatcgg tctttcttta | 960 |
| tttcaagagt ccagaaatgg caacattacc tttgattcaa tgtaatggaa agagctcttt | 1020 |
| caagagacag agaaaagaat aatttaattt ctttccccac acctccttcc ctgtctctta | 1080 |
| ccctatcttc cttccttcta ccctccccat ttctctctct catttctcag aagtatattt | 1140 |
| tgaaaggatt catagcagac agctaaggct ggttttttct aagtgaagaa gtgatattga | 1200 |
| gaaggtaggg ttgcatgagc cctttcagtt ttttagttta tatacatctg tattgttaga | 1260 |
| atgttttata atataaataa aattatttct cagttatata ctagctatgt aacttgtgga | 1320 |
| tatttcctta agtattacaa gctatactta actcacttgg aaaactcaaa taaatacctg | 1380 |
| cttcatagtt attaataagg attaagtgag ataatgccca taagattcct attaataaca | 1440 |
| gataaataca tacacacaca cacacattga aaggattctt actttgtgct aggaactata | 1500 |
| ataagttcat tgatgcatta tatcattaag ttctaatttc aacactagaa ggcaggtatt | 1560 |
| atctaaattt catactggat acctccaaac tcataaagat aattaaattg ccttttgtca | 1620 |
| tatatttatt caaaagggta aactcaaact atggcttgtc taattttata tatcacccta | 1680 |

-continued

```
ctgaacatga ccctattgtg atattttata aaattattct caagttatta tgaggatgtt      1740
gaaagacaga gaggatgggg tgctatgccc caaatcagcc tcacaattaa gctaagcagc      1800
taagagtctt gcagggtagt gtagggacca cagggttaag ggggcagtag aattatactc      1860
ccactttagt ttcatttcaa acaatccata cacacacagc cctgagcact acaaattat       1920
actacgctct atacttttg tttaaatgta taaataagtg gatgaaagaa tagatagata       1980
gacagataga tgatagatag aataaatgct tgccttcata gctgtctccc taccttgttc      2040
aaaatgttcc tgtccagacc aaagtacctt gccttcactt aagtaatcaa ttcctaggtt      2100
atattctgat gtcaaaggaa gtcaaagat gtgaaaaaca atttctgacc cacaactcat       2160
gctttgtaga tgactagatc aaaaaatttc agccatatct taacagtgag tgaacaggaa      2220
atctcctctt ttccctacat ctgagatccc agcttctaag accttcaata ctcactcttg      2280
atgcaacaga ccttggaagt atacaggaga gctgaacttg gtcaacaaag gagaaaagtt      2340
tgttggcctc caaaggcaca gctcaaactt ttcaagcctt ctctaatctt aaaggtaaac      2400
aagggtctca tttctttgag aacttcaggg aaaatagaca aggacttgcc tggtgctttt      2460
ggtaggggag cttgcacttt ccccctttct ggaggaaata tttatcccca ggtagttccc      2520
tttttgcacc agtggttctt tgaagagact tccacctggg aacagttaaa cagcaactac      2580
agggccttga actgcacact ttcagtccgg tcctcacagt tgaaaagacc taagcttgtg      2640
cctgatttaa gcctttttgg tcataaaaca ttgaattcta atctccctct caaccctaca      2700
gtcacccatt tggtatatta aagatgtgtt gtctactgtc tagtatccct caagtagtgt      2760
caggaattag tcatttaaat agtctgcaag ccaggagtgg tggctcatgt ctgtaattcc      2820
agcactggag aggtagaagt gggaggactg cttgagctca agagtttgat attatcctgg      2880
acaacatagc aagacctcgt ctctacttaa aaaaaaaaaa attagccagg catgtgatgt      2940
acacctgtag tccccagcta ctcaggagg                                        2969
```

<210> SEQ ID NO 42
<211> LENGTH: 1448
<212> TYPE: DNA
<213> ORGANISM: Artificial Sequence
<220> FEATURE:
<223> OTHER INFORMATION: EGFR(ER2) antibody heavy chain

<400> SEQUENCE: 42

```
cggccgccag tgtgctggaa ttcacattca cgatgtactt gggactgaac tatgtattca       60
tagtttttct cttaaatggt gtccagagtg aggtgcagct ggtggagtct gggggaggcg      120
tggtacagcc tggagggtcc ctgagactct cctgtgcagc ctctggattc accttcagtg      180
actacgacat gagctggatc cgccaggctc caggaagggg ctggagtgg gtctcaggga      240
tccttggtgg tagtgagcgt tcgtactata gggactccgt gaagggccgg ttcaccatct      300
ccagagacaa ttccaggaaa accctgtatc tgcaaatgaa cagcctgaga gccgaggaca      360
cggctgtgta ttactgtgcg agacacggca gcccgggata cacgttgtat gcgtgggact      420
actggggcca aggaccacgg tcaccgtctc ctcagcctc caccaagggc ccatcggtct      480
tccccctggc accctcctcc aagagcacct ctggggggcac agcggccctg gctgcctgg       540
tcaaggacta cttccccgaa ccggtgacgg tgtcgtggaa ctcaggcgcc ctgaccagcg      600
gcgtgcacac cttcccggct gtcctacagt cctcaggact ctactccctc agcagcgtgg      660
tgaccgtgcc ctccagcagc ttgggcaccc agacctacat ctgcaacgtg aatcacaagc      720
```

```
ccagcaacac caaggtggac aagaaagttg agcccaaatc ttgtgacaaa actcacacat    780
gcccaccgtg cccagcacct gaactccttg ggggaccgtc agtcttcctc ttccccccaa    840
aacccaagga caccctcatg atctcccgga cccctgaggt cacatgcgtg gtggtggacg    900
tgagccacga agaccctgag gtcaagttca actggtacgt ggacggcgtg gaggtgcata    960
atgccaagac aaagccgcgg gaggagcagt acaacagcac gtaccgtgtg gtcagcgtcc   1020
tcaccgtcct gcaccaggac tggctgaatg gcaaggagta caagtgcaag gtctccaaca   1080
aagccctccc agcccccatc gagaaaacca tctccaaagc caagggcagc cccgagaac    1140 cacaggtgta caccctgccc ccatcccggg atgagctgac caagaaccag gtcagcctga   1200
cctgcctggt caaaggcttc tatcccagcg acatcgccgt ggagtgggag agcaatgggc   1260
agccggagaa caactacaag accacgcctc ccgtgctgga ctccgacggc tccttcttcc   1320
tctacagcaa gctcaccgtg gacaagagca ggtggcagca ggggaacgtc ttctcatgct   1380
ccgtgatgca tgaggctctg cacaaccact acacgcagaa gagcctctcc ctgtctccgg   1440
gtaaatag                                                            1448
```

<210> SEQ ID NO 43
<211> LENGTH: 729
<212> TYPE: DNA
<213> ORGANISM: Artificial Sequence
<220> FEATURE:
<223> OTHER INFORMATION: ER2 antibody light chain

<400> SEQUENCE: 43

```
cggagcaaga tggattcaca ggcccaggtt cttatgttac tgctgctatg ggtatctggt     60
acctgtgggg atattgtgat gacccagact ccactctccc tgcccgtcac ccctggagag    120
ccggcctcca tctcatgcag gtctaatcag gacttgaccc atagtaacgg aaacacctat    180
ttggagtggt acctgcagaa gccagggcag tctccaagac tcctaattta aggtttct     240 aaccggttct ctggggtccc agacagattc agtggcagtg gggcaggtac agatttcaca    300
ctgagaatca gcagggtgga agctgaggat gttgggtttt attactgcat gcaaggtaca    360
cactggccgt ggacgttcgg ccaagggacc aaggtggata tcaaacgtac tgtggctgca    420
ccatctgtct tcatcttccc gccatctgat gagcagttga aatctggaac tgcctctgtt    480
gtgtgcctgc tgaataactt ctatcccaga gaggccaaag tacagtggaa ggtggataac    540
gccctccaat cgggtaactc ccaggagagt gtcacagagc aggacagcaa ggacagcacc    600
tacagcctca gcagcaccct gacgctgagc aaagcagact acgagaaaca caaagtctac    660
gcctgcgaag tcacccatca gggcctgagc tcgcccgtca caaagagctt caacagggg    720 gagtgttag                                                           729
```

<210> SEQ ID NO 44
<211> LENGTH: 25
<212> TYPE: DNA
<213> ORGANISM: Artificial Sequence
<220> FEATURE:
<223> OTHER INFORMATION: PCR forward primer for deleted from of human
      complement factor H(dCFH)

<400> SEQUENCE: 44

```
actcgaggta agtatcaagg ttaca                                           25
```

<210> SEQ ID NO 45
<211> LENGTH: 25
<212> TYPE: DNA

<213> ORGANISM: Artificial Sequence
<220> FEATURE:
<223> OTHER INFORMATION: PCR reverse primer for deleted from of human complement factor H(dCFH)

<400> SEQUENCE: 45
actcgagctg tggagagaaa ggcaa                                         25

<210> SEQ ID NO 46
<211> LENGTH: 1524
<212> TYPE: DNA
<213> ORGANISM: Artificial Sequence
<220> FEATURE:
<223> OTHER INFORMATION: deleted from of human complement factor H (dCFH)

<400> SEQUENCE: 46
atgagacttc tagcaaagat tatttgcctt atgttatggg ctatttgtgt agcagaagat    60
tgcaatgaac ttcctccaag aagaaataca gaaattctga caggttcctg gtctgaccaa   120
acatatccag aaggcaccca ggctatctat aaatgccgcc tggatatag atctcttgga    180 aatataataa tggtatgcag aagggagaa tgggttgctc ttaatccatt aaggaaatgt    240
cagaaaaggc cctgtggaca tcctggagat actcctttg gtacttttac ccttacagga    300
ggaaatgtgt tgaatatgg tgtaaaagct gtgtatacat gtaatgaggg gtatcaattg    360
ctaggtgaga ttaattaccg tgaatgtgac acagatggat ggaccaatga tattcctata   420
tgtgaagttg tgaagtgttt accagtgaca gcaccagaga atggaaaaat tgtcagtagt   480
gcaatggaac cagatcggga ataccatttt ggacaagcag tacggtttgt atgtaactca   540
ggctacaaga ttgaaggaga tgaagaaatg cattgttcag acgatggttt ttggagtaaa   600
gagaaaccaa agtgtgtgga aatttcatgc aaatccccag atgttataaa tggatctcct   660
atatctcaga agattatttta aaggagaat gaacgatttc aatataaatg taacatgggt   720
tatgaataca gtgaaagagg agatgctgta tgcactgaat ctggatggcg tccgttgcct   780
tcatgtgaag aaaaatcatg tgataatcct tatattccaa atggtgacta ctcaccttta   840 aggattaaaac acagaactgg agatgaaatc acgtaccagt gtagaaatgg tttttatcct   900
gcaaccgggg aaatacagc caaatgcaca agtactggct ggatacctgc tccgagatgt   960
gacacctcct gtgtgaatcc gcccacagta caaatgctt atatagtgtc gagacagatg  1020
agtaaatatc catctggtga gagtacgt tatcaatgta ggagccctta tgaaatgtt t  1080 ggggatgaag aagtgatgtg tttaaatgga aactggacgg aaccacctca atgcaaagat  1140
tctacaggaa aatgtgggcc ccctccacct attgacaatg gggacattac ttcattcccg  1200
ttgtcagtat atgctccagc ttcatcagtt gagtaccaat gccagaactt gtatcaactt  1260
gagggtaaca agcgaataac atgtagaaat ggacaatggt cagaaccacc aaaatgctta  1320
catccgtgtg taatatcccg agaaattatg gaaaattata acatagcatt aaggtggaca  1380
gccaaacaga agctttattc gagaacaggt gaatcagttg aatttgtgtg taacgggga   1440 tatcgtcttt catcacgttc tcacacattg cgaacaacat gttgggatgg gaaactggag  1500
tatccaactt gtgcaaaaag atag                                        1524

<210> SEQ ID NO 47
<211> LENGTH: 29
<212> TYPE: DNA
<213> ORGANISM: Artificial Sequence
<220> FEATURE:
<223> OTHER INFORMATION: PCR forward primer (pMSGneo-hCHF)

```
<400> SEQUENCE: 47
tagcggccgc catgagactt ctagcaaag                                        29

<210> SEQ ID NO 48
<211> LENGTH: 30
<212> TYPE: DNA
<213> ORGANISM: Artificial Sequence
<220> FEATURE:
<223> OTHER INFORMATION: PCR reverse primer (pMSGneo-hCHF)

<400> SEQUENCE: 48
cgcctcgagc tatcttttg cacaagttgg                                        30

<210> SEQ ID NO 49
<211> LENGTH: 21
<212> TYPE: DNA
<213> ORGANISM: Artificial Sequence
<220> FEATURE:
<223> OTHER INFORMATION: PCR forward primer

<400> SEQUENCE: 49
atgcagcgcg tgaacatgat c                                                21

<210> SEQ ID NO 50
<211> LENGTH: 23
<212> TYPE: DNA
<213> ORGANISM: Artificial Sequence
<220> FEATURE:
<223> OTHER INFORMATION: PCR reverse primer

<400> SEQUENCE: 50
ccaatgaatt aaccttggaa atc                                              23

<210> SEQ ID NO 51
<211> LENGTH: 34
<212> TYPE: DNA
<213> ORGANISM: Artificial Sequence
<220> FEATURE:
<223> OTHER INFORMATION: PCR forward primer (pMS-FIX)

<400> SEQUENCE: 51
ctagctagcc accatgcagc gcgtgaacat gatc                                  34

<210> SEQ ID NO 52
<211> LENGTH: 33
<212> TYPE: DNA
<213> ORGANISM: Artificial Sequence
<220> FEATURE:
<223> OTHER INFORMATION: PCR reverse primer (pMS-FIX)

<400> SEQUENCE: 52
gaagatcttc attaagtgag ctttgttttt tcc                                   33
```